United States Patent
Tsang et al.

(10) Patent No.: US 7,101,546 B2
(45) Date of Patent: Sep. 5, 2006

(54) IN SITU MATURATION OF CULTURED PANCREATIC STEM CELLS HAVING A SPECIFIED, INTERMEDIATE STAGE OF DEVELOPMENT

(75) Inventors: Wen-Ghih Tsang, Sherman Oaks, CA (US); Tianli Zheng, Culver City, CA (US); Yanping Wang, Los Angeles, CA (US)

(73) Assignee: AmCyte, Inc., Santa Monica, CA (US)

( * ) Notice: Subject to any disclaimer, the term of this patent is extended or adjusted under 35 U.S.C. 154(b) by 457 days.

(21) Appl. No.: 10/326,190

(22) Filed: Dec. 20, 2002

(65) Prior Publication Data

US 2003/0170215 A1 Sep. 11, 2003

Related U.S. Application Data

(60) Provisional application No. 60/342,250, filed on Dec. 21, 2001.

(51) Int. Cl.
*A61K 35/39* (2006.01)
*C12N 5/06* (2006.01)
*C12N 5/00* (2006.01)
*C12N 5/08* (2006.01)

(52) U.S. Cl. .................... 424/93.7; 435/347; 435/373; 435/375; 435/402

(58) Field of Classification Search .................. None
See application file for complete search history.

(56) References Cited

U.S. PATENT DOCUMENTS

| | | |
|---|---|---|
| 5,550,178 A | 8/1996 | Desai et al. |
| 5,578,314 A | 11/1996 | Cochrum |
| 5,739,033 A | 4/1998 | Soon-Shiong |
| 5,762,959 A | 6/1998 | Soon-Shiong et al. |
| 5,874,306 A | 2/1999 | Beattie et al. |
| 5,888,816 A | 3/1999 | Coon et al. |
| 5,928,942 A | 7/1999 | Brothers |
| 6,001,647 A | 12/1999 | Peck et al. |
| 6,759,039 B1 | 7/2004 | Tsang et al. |
| 2001/0000324 A1 | 4/2001 | Todorov et al. |

FOREIGN PATENT DOCUMENTS

| | | |
|---|---|---|
| WO | WO 97/15310 | 5/1997 |
| WO | WO 99/61586 A1 | 12/1999 |
| WO | WO 00/47721 A2 | 8/2000 |
| WO | WO 00/78929 A1 | 12/2000 |

OTHER PUBLICATIONS

Definition of "in situ." Merriam-Webster Medical Dictionary@ Medline. Accessed Oct. 18, 2005.*

Lim F et al. 1980. Microencapsulated islets as bioartificial endocrine pancreas. Science 210: 908-910.*

Bonner-Weir, S., et al., "In vitro cultivation of human islets from expanded ductal tissue," *PNAS*, 97(14):7999-8004 (Jul. 5, 2000).

Gmyr, V., et al., "Adult Human Cytokeratin 19-Positive Cells Reexpress Insulin Promoter Factor 1 In Vitro Further Evidence for Pluripotent Pancreatic Stem Cells in Humans," *Diabetes*, 49:1671-1680 (Oct. 2000).

Peck, A. B., et al., "Pancreatic stem cells: building blocks for a better surrogate islet to treat type 1 diabetes," *Ann Med.* 33:186-192 (2001).

Shapiro, A. M. J., et al., "Islet Transplantation in Seven Patients with Type 1 Diabetes Mellitus Using a Glucocorticoid-Free Immunosuppressive Regimen," *New England J. of Med.*, 343:230 (Jul. 27, 2000).

Soon-Shiong, P., et al., "Long-term reversal of diabetes by the injection of immunoprotected islets," *Proc. Natl. Acad. Sci. USA*, 90:5843-5847 (Jun. 1993).

Stephan, J. -P., et al., "Selective Cloning of Cell Surface Proteins Involved in Organ Development: Epithelial Glycoprotein is Involved in Normal Epithelial Differentiation," *Endocrinology*, 140(12):5841-5854 (1999).

Zhou, Y. -T., et al., "Leptin Normalizes the Impaired Response of Proinsulin mRNA to Long Chain Fatty Acids in Heterozygous Zucker Diabetic Fatty Rats," *J. Biol. Chem*, 242(41):25648-25651 (1997).

Zulewski, H., et al., "Multipotential Nestin-Positive Stem Cells Isolated from Adult pancreatic Islets Differentiate Ex Vivo Into Pancreatic Endocrine, Exocrine, and Hepatic Phenotypes," *Diabetes*, 50:521-533 (Mar. 2001).

van Schelfgaarde, "Factors influencing the properties and performance of microcapsules for immunoprotection of pancreatic islets" *J. Mol. Med* 77: 199-205 (1999).

Uludag et al., "Technology of mammalan cell encapsulation" *Adv. Drug Del Rev.* 42:29-64 (2000).

Carlsson et al., "Engraftment and Growth of Transplanted Pancreatic Islets" *Ups J. Med Sci* 105(2):107-123 (2000).

Soon-Shiong et al., "Insulin independence in a type 1 diabetic patient after encapsulate islet transplantation", *Lancet* 343:950-951 (1994).

* cited by examiner

*Primary Examiner*—Sandra E. Saucier
*Assistant Examiner*—Lora E Barnhart
(74) *Attorney, Agent, or Firm*—Townsend and Townsend and Crew LLP

(57) ABSTRACT

This invention relates to the discovery that an intermediate, differentiated stage of pancreatic stem cells exist that can be matured in situ into a stable cell line that produces insulin in response to glucose. These cells are advantageous in that they are both expandable and stable in culture. This invention avoids the step of culturing the intermediate stage stem cells into later stage pancreatic cells.

4 Claims, 8 Drawing Sheets

IN SITU MATURATION OF CULTURED PANCREATIC STEM CELLS HAVING A SPECIFIED, INTERMEDIATE STAGE OF DEVELOPMENT

CROSS-REFERENCES TO RELATED APPLICATIONS

This application claims the benefit of provisional application No. 60/342,250 filed Dec. 21, 2001, the contents of which are incorporated by reference herein for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

This invention relates to the discovery that an intermediate, differentiated stage of pancreatic stem cells exist that can be encapsulated and matured under in situ conditions to produce a stable culture of cells that produce insulin production in response to glucose. These cells are valuable in that they are both expandable and stable in culture and can be driven to late stage development. This invention avoids the step of in vitro culturing these intermediate differentiated stage cells into late stage pancreatic cells.

BACKGROUND OF THE INVENTION

The mammalian pancreas develops from the embryonic foregut bud. As the embryonic buds grow, a ductal system develops by branching morphogenesis. After the ventral and dorsal anlage fuse, the new organ grows and matures into two interlocked structures, the exocrine system and the endocrine system. The majority of the pancreas is composed of acinar cells that produce digestive enzymes. The endocrine system includes β-cells, which produce insulin, α-cells, which produce glucagon, and δ-cells, which produce somatostatin. The endocrine cells are organized into clusters called islets.

Animal research has shown at least two mechanisms of β-cell formation: neogenesis from ductal precursor cells and replication of mature β-cells. Replication of differentiated β-cells is maintained postnatally into adulthood. Replication of β-cells is accelerated by an increased demand for insulin, for example, as a result of high glucose infusion, partial pancreatectomy, and during gestation. Under these conditions, β-cells mass quickly increases through both cell hypertrophy (enlargement of volume of individual cells) and hyperplasia (increase in the number of β-cells).

In Type I or insulin dependent diabetes mellitus (IDDM) there is a clear reduction in the number of β-cells due to an autoimmune attack against the β-cells. Eisenbarth, *N. Eng. J. Med.* 314:1360–1368 (1986). A treatment for Type I diabetes could include increasing in the number of β-cells in a subject suffering from Type I diabetes. Bonner-Weir, *Endocrin.* 141:1926–1929 (2000).

Another treatment for diabetes using islet cells involves grafting pancreatic tissue from immune matched donors into transplant recipients. Typically, transplant recipients are required to receive immunosuppressant therapy to prevent rejection of the transplanted organ. Recently developed immunosuppressant regimens have improved the results of clinical islet transplantation in humans. While the technique remains experimental, if islet cell transplants can perform the same function as whole organ pancreas grafts, this much simpler surgical procedure would play an important role in the treatment of diabetes.

Although the transplantation of human islets shows promise as a powerful treatment for diabetes, a number of impediments exist that presently limit the utility of this procedure. One significant impediment is the inability to produce sufficient numbers of islet cells for use in the procedure. Presently, the process used to obtain islets for transplantation typically involves isolation of pancreatic tissue, enzymatic digestion of the pancreatic tissue to liberate the individual cells from the surrounding tissue, and the use of a gradient centrifugation purification technique. The gradient centrifugation purification technique is well known in the art and is performed by many islet transplant centers. Unfortunately, the yield of islets from a single pancreas treated with the standard procedure is usually insufficient for transplantation. Accordingly, alternatives to this procedure have been sought and developed.

A method to selectively propagate intermediate stage pancreatic stem cells has been developed. Briefly, after isolation from donor pancreas, cells are allowed to recover in high serum media and are then switched to low serum media to promote the growth of intermediate stage pancreatic stem cells. These cells can be matured into insulin secreting cell aggregates by growth to confluence on conditioned culture dishes. However, these aggregated cells are of limited clinical use, because if transplanted directly, the cells may raise a detrimental immune response in the host.

DESCRIPTION OF THE DRAWINGS

FIG. 1 shows encapsulated proliferated P3 aggregates before transplantation. The cells were immunostained for (A) CK19-1, (B) Insulin, (C) Glucagon, and (D) Somatostatin. The magnification is 60×.

FIG. 2 shows blood glucose levels in an SCID mouse before and after transplantation of 105 HD394i, P3 cells in 200 liquid capsules.

FIG. 3 shows encapsulated prolifereated P3 aggregates after removal from an animal. The cells were stained with antibodies specific for insulin. The following magnifications are shown: (A) Area 1, 4×; (B) Area 1, 10×; (C) Area 1, 60×; (D) Area 2, 10×; (E) Area 2, 60×; (F) Area 2, 60×.

FIG. 4 shows encapsulated isolated islets after 6 months in culture immunostained for (A) CK19-1, (B) PDX-1, (C) Insulin, (D) Glucagon, and (E) Somatostatin. The magnification was 60×.

FIG. 5 shows encapsulated isolated islets after 28 months in culture immunostained for (A) CK19-1, (B) PDX-1, (C) Insulin, (D) Glucagon, (E) Somatostatin, and (F) Amylase. The magnification was 60×.

FIG. 6 shows Blood glucose levels in nude rats before and after transplantation of 4,000 encapsulated HD357 islets (in 200 capsules), which had been maintained in culture for more than nine months. One hundred grafted capsules were retrieved on day 118.

FIG. 7 shows the results of oral glucose tolerance tests in recipients of 4,000 encapsulated HD357 islets (in 200 capsules). The test was done 35 days after transplantation.

FIG. 8 shows protein expression in native human pancreas. Samples were immunostained for the following proteins: (A) CK-19, (B) PDX-1(C) Insulin, (D) Glucagon, (E) Amylase. The magnification was 60×.

SUMMARY OF THE INVENTION

Figure 1:
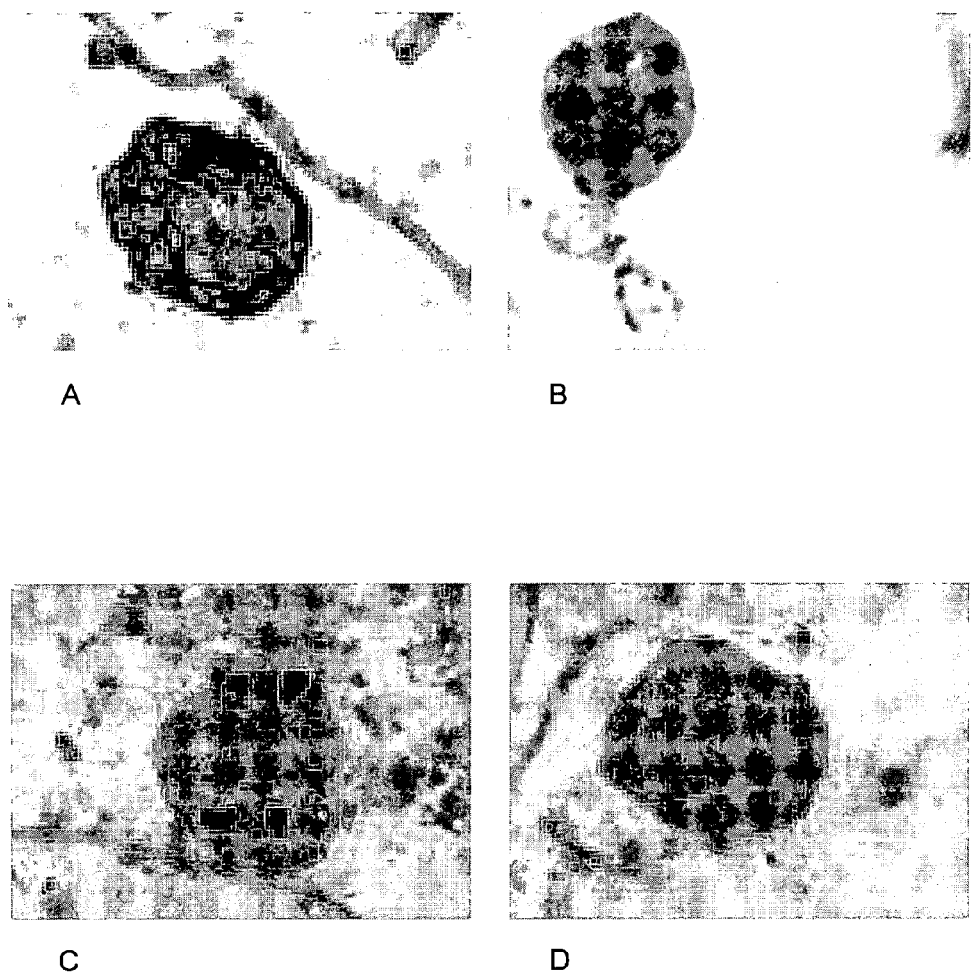
FIG. 1.

This invention provides an in situ method of providing insulin to a mammal by encapsulating a cell culture of propagating pancreatic cells with the following properties: (i) the cells can be passed from one culture vessel to a second vessel at an initial concentration of about 180 cells per square centimeter and expanded to about 1,800 cells per square centimeter, and (ii) both the unexpanded and expanded cells are 90% PDX-1 positive and have an insulin:actin mRNA ratio of between 1:100 and 1000:1. After encapsulation, the cells are transplanted or implanted into a mammal permitting the cells to mature to insulin secreting cells.

In one embodiment, the cells mature into an aggregate of cells. the cellular aggregate has a mantle of CK19-positive cells and an inner cell mass of between 50–5000 pancreatic cells and has a diameter of between 50 and 300 microns. In another embodiment of the invention, the mammal is a diabetic human.

In one aspect of the invention, the cell culture has an insulin:actin mRNA ratio of between 1:10 and 100:1.

In another embodiment, the encapsulation includes the following steps: surrounding the cells with alginate to make a capsule, cross-linking the alginate with a divalent cation, and providing a polylysine membrane to enclose the capsule.

In a further embodiment, the invention provides encapsulated pancreatic cells with the following properties: (i) the ability to proliferate, and (ii) both the unexpanded and expanded cells are 90% PDX-1 positive and have an insulin:actin mRNA ratio of between 1:100 and 1000:1.

DEFINITIONS

"Encapsulation" refers to a process where cells are surrounded by a biocompatible acellular material, such as sodium alginate and polylysine. Preferably small molecules, like sugars and low molecular weight proteins, can be taken up from or secreted into an environment surrounding the encapsulated cells. At the same time access to the encapsulated cells by larger molecules and immune cells is limited.

"In situ" refers to cell maturation or growth while encapsulated. In situ growth or maturation can take place in while in a culture vessel or after implantation into an animal. "Mature" or "maturation" refers to a process where cells progress from an undifferentiated state to a differentiated state. For example, undifferentiated pancreatic cells are able to proliferate and express characteristics markers, like PDX-1. Mature pancreatic cells do not proliferate and secrete high levels of pancreatic endocrine hormones. E.g., mature β-cells secrete insulin at high levels. Changes in cell interaction and maturation occur as cells lose markers of undifferentiated cells or gain markers of differentiated cells. Loss or gain of a single marker can indicate that a cell has "matured."

"Aggregate" in the context of cells refers to a three dimensional structure.

"CK-19" is a 40 Kd acidic keratin, cytokeratin 19.

"Insulin:actin mRNA ratios are measured by band density using gel scanner or by real time PCR using different labels for insulin and actin. It is an average across a population of cells.

"Implanting" is the grafting or placement of the cells into a recipient. It includes encapsulated cells and non-encapsulated. The cells can be placed subcutaneously, intramuscularly, intraportally or interperitoneally by methods known in the art.

"Passage" of cells growing as a monolayer attached to a surface usually refers to a transition of a seeded culture container from a partially confluent state to a confluent state, at which point they are removed from the culture container and reseeded in a culture container at a lower density. However, cells may be passaged prior to reaching confluence. Passage typically results in expansion of the cell population as they grow to reach confluence. The expansion of the cell population depends on the initial seeding density but is typically a 1 to 10, 1 to 5, 1 to 3, or 1 to 2 fold expansion. Thus, passaging generally requires that the cells be capable of a plurality of cell divisions in culture.

A "population" of cells refers to a plurality of cells obtained by a particular isolation or culture procedure. While the selection processes of the present invention yield populations with relatively uniform properties, a population of cells may be heterogenous when assayed for marker expression or other phenotype. Properties of a cell population are generally defined by a percentage of individual cells having the particular property (e.g., the percentage of cells staining positive for a particular marker) or the bulk average value of the property when measured over the entire population (e.g., the amount of mRNA in a lysate made from a cell population).

"90% PDX-1 positive" refers to a statistical sampling of randomly selected cells. Standard immunochemistry techniques are used and positively stained cells are counted visually under a microscope. Percentage is determined by comparison with appropriately controlled samples, i.e., preparing identical cells and using an antibody of similar isotype but not specific for PDX-1.

"Serum" refers to material obtained from blood other than blood cells. Serum is typically obtained by clotting or by physical separation of blood cells by centrifugation and defibrination. As used herein, serum may be functionally defined by its biological activity: serum generally supports the growth of mammalian cells in culture when added to culture media. Serum may be obtained from a variety of species (e.g., human, bovine, ovine, equine, porcine, rabbit, chicken, and the like) and developmental stages (e.g., fetus, juvenile, or adult). In certain embodiments, "serum" also refers to serum supplement or replacement products obtained from fractionated serum or other sources, e.g. Select Soytone (Becton Dickinson) or other commercially available products. Such serum equivalents may be completely or partially defined.

"Mantle" refers to an envelope of cells surrounding in three dimensions the inner cell mass.

DETAILED DESCRIPTION

This invention relates to the discovery that an intermediate, differentiated stage of pancreatic stem cells exists and that the pancreatic stem cells can be matured into insulin producing aggregates while encapsulated. These pancreatic stem cells recapitulate the cellular architecture and function of encapsulated islets isolated directly from pancreas. The pancreatic stem cells provide the benefit of being expandable in culture, while the encapsulation procedure allows control over the size and number of cells with the aggregate.

I. Methods of Isolating Pancreatic Cells

The present invention provides methods to induce maturation of a population of intermediate stage pancreatic stem cells into an insulin secreting cell aggregate. Typically, as an initial step the intermediate stage pancreatic stem cells are isolated from the pancreas. Cells harvested from a pancreas are a diverse population that may yield differentiated cells capable of endocrine and exocrine secretion. These differentiated cells express pancreatic endocrine molecules such as insulin, somatostatin, glucagon and other endocrine hormones, as well as pancreatic exocrine molecules such as amylase. Further, a portion of the cultured cell population is capable of replication and expansion in culture. This intermediate stage pancreatic stem cell population used in the present invention can thus be isolated from donor pancreas. Freshly isolated pancreatic cells are then cultured under conditions to promote the growth of intermediate stage pancreatic stem cells.

A. Donor Source

The donor source can be one or more donor pancreases, from cultured pancreatic cells, or other sources capable of yielding cells that are capable of producing pancreatic endocrine and exocrine hormones. In a preferred embodiment, the cells isolated for subsequent culturing are obtained from one or more donated pancreases. The methods described herein are not dependent on the age of the donated pancreas. Accordingly, pancreatic material isolated from donors ranging in age from embryos to adults can be used.

In another embodiment, pancreatic cells are isolated from a cultured source. For example, cells prepared according to the microencapsulation method of U.S. Pat. No. 5,762,959 to Soon-Shiong, et al., entitled "Microencapsulation of cells," can be harvested as a source of donor cells.

B. Isolation of Pancreatic Cell Populations

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissected into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations (see U.S. Pat. Nos. 5,830,741 and 5,753,485) and other enzymes are contemplated for use with the methods disclosed herein.

Isolated source material can be further processed to enrich for one or more desired cell populations. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e.g., NYCODENZ®, FICOLL®, or PERCOLL®). For example the gradient method described in U.S. Pat. No. 5,739,033, can be used as a means for enriching the processed pancreatic material in islets. The mixture of cells harvested from the donor source will typically be heterogeneous and thus contain α-cells, β-cells, δ-cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is islet-enriched and typically contains 10 to 100% islet cells in suspension. The second interface is typically a mixed population of cells containing islets, acinar, and ductal cells. The bottom layer is the pellet, which is formed at the bottom of the gradient. This layer typically contains primarily (>80%) acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation. When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one embodiment, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped cells, respectively, can also be used in culture. While both layers contain cells capable of giving rise to the intermediate stage population described herein, each layer may have particular advantages for use with the disclosed methods.

II. Generation and Propagation of an Intermediate Stage Pancreatic Stem Cell Population

A. General Cell Culture Procedures

Once the pancreatic cells are obtained and isolated, they are cultured under conditions that select for propagation of the desired intermediate stage population, or in other embodiments, for the differentiation of more mature cell types. General cell culture methodology may be found in Freshney, *Culture of Animal Cells: A Manual of Basic Technique* 4th ed., John Wiley & Sons (2000). Typically, pancreatic cells are cultured under conditions appropriate to other mammalian cells, e.g., in humidified incubators at 37° C. in an atmosphere of 5% $CO_2$. Cells may be cultured on a variety of substrates known in the art, e.g., borosilicate glass tubes, bottles, dishes, cloning rings with negative surface charge, plastic tissue culture tubes, dishes, flasks, multi-well plates, containers with increased growth surface area (GSA) or Esophageal Doppler Monitor (EDM) finish, flasks with multiple internal sheets to increase GSA, Fenwal bags, and other culture containers.

Once the pancreatic cellular material has been harvested and selected for culture, or once a population is confluent and is to be transferred to a new substrate, a population of cells is seeded to a suitable tissue culture container for cultivation. Seeding densities can have an effect on the viability of the pancreatic cells cultured using the disclosed methods, and optimal seeding densities for a particular culture condition may be determined empirically by seeding the cells at a range of different densities and monitoring the resulting cell survival and proliferation rate. A range of seeding densities have been shown to be effective in producing hormone secreting cells in culture. Typically, cell concentrations range from about $10^2$ to $10^8$ cells per 100 mm culture dish, e.g., $10^2$, $10^3$, $10^4$, $10^5$, $10^6$, $10^7$, or $10^8$ cells per 100 mm culture dish, although lower cell concentrations may be employed for cloning procedures. Cell concentration for other culture vessels may be adjusted by computing the relative substrate surface area and/or medium gas exchange surface area for a different culture vessel. For example, a typical 100 mm culture dish has a substrate surface area of 55 square centimeters (see Freshney, supra), and a cell concentration of 10,000 cells per dish corresponds to about 180 cells per square centimeter, while a cell concentration of 100,000 cells per dish corresponds to about 1,800 cells per square centimeter. Cell concentration in terms of culture vessel surface area may be related to cell concentration in terms of media volume by using the appropriate media volume per culture surface area (0.2–0.5 ml/cm$^2$ are typical ranges for static culture). To determine if a 10 fold expansion has occurred, the cells are removed by enzymatic digestion and counted under microscope in a known volume of fluid. Cells may also be grown on culture surfaces pre-coated with defined extracellular matrix components to encourage growth and differentiation (e.g., fibronectin, Collagen I, Engelbreth-Holm-Swarm matrix, and, preferably, collagen IV or laminin).

Standard cell culture propagation techniques are suitable for practice of the invention. When cells are growing attached to a culture surface, they are typically grown as a monolayer until 80%–90% confluence is reached, at which point the cells are released from the surface by proteolytic digestion and split 1:2 or 1:3 for culture in new vessels. Higher dilutions of the cells are also suitable, generally between the range of 1:4 to 1:10, although even lower cell concentrations are appropriate in cloning procedures. Concentrations of proteolytic enzymes and chelating agents are usually lowered when cells are passaged in serum-free media (e.g., 0.025% trypsin and 0.53 mM EDTA). Culture medium is typically changed twice weekly or when the pH of the medium indicates that fresh medium is needed.

The pancreatic cells of the present invention may be cultured in a variety of media. As described herein, media containing or lacking particular components, especially serum, are preferred for certain steps of the isolation and propagation procedures. For example, cells freshly isolated from the pancreas may be maintained in high-serum medium to allow the cells to recover from the isolation procedure. Conversely, low-serum medium favors the selection and propagation of an intermediate stage population. Accordingly, a number of media formulations are useful in the practice of the invention. The media formulations disclosed here are for exemplary purposes, and non-critical components of the media may be omitted, substituted, varied, or added to simply by assaying the effect of the variation on the replication or differentiation of the cell population, using the assays described herein. See, e.g., Stephan et al., *Endocrinology* 140:5841–54 (1999)).

Culture media usually comprise a basal medium, which includes inorganic salts, buffers, amino acids, vitamins, an energy source, and, in some cases, additional nutrients in the form of organic intermediates and precursors that are involved in protein, nucleic acid, carbohydrate, or lipid metabolism. Basal media include F12, Eagle's MEM, Dulbecco's modified MEM (DMEM), RPMI 1640, a 1:1 mixture of F12 and DMEM, and others. See Freshney, supra. To support the growth of cells, basal medium is usually supplemented with a source of growth factors, other proteins, hormones, and trace elements. These supplements encourage growth, maintenance, and/or differentiation of cells, compensate for impurities or toxins in other medium components, and provide micronutrients lacking in the basal medium. In many culture media, serum is the source of these supplements. Serum can be supplied from a variety of mammalian sources, such as human, bovine, ovine, equine, and the like, and from adult, juvenile, or fetal sources. See Freshney, supra. Fetal bovine serum is a commonly used supplement. Concentrations of serum are expressed in terms of volume of serum as a percentage of the total medium volume, and typically range from about 0.1 to 25%, e.g., about 0.1, 0.2, 0.5, 1, 2, 3, 4, 5, 6, 7, 8, 9, 10, 15, 20, or 25%. In some applications, the basal medium is supplemented with defined or semi-defined mixtures of growth factors, hormones, and micronutrients, rather than with serum. Formulas for serum replacement supplements are disclosed herein; others are known in the art or available from commercial sources (see Freshney, supra). For some embodiments, the concentration of serum is lowered but not eliminated, and defined or semi-defined supplement mixtures are added to the basal medium. Preferred applications for media containing high or low concentrations of serum are described herein.

B. Maintenance and Propagation of Isolated Pancreatic Cells in High Serum

Cells harvested from a donor pancreas have usually undergone a period of warm or cold ischemia between the death of the donor and the beginning of the isolation procedure. Moreover, during the isolation procedure, pancreatic cells are usually subjected to proteolytic digestion as well as mechanical and shear stresses. Without wishing to be bound by a particular theory, the various traumas experienced by these cells may up-regulate various cellular processes that result in the expansion of pancreatic stem cell populations, such as facultative progenitor cells. Intermediate cell populations may be generated with satisfactory efficiency by placing cells into low-serum media directly after isolation or purification. Nonetheless, because the trauma experienced by cells during the isolation procedures may have adverse effects on cell survival and adaptation to culture, it is sometimes desirable to maintain the freshly isolated cells in a stabilizing medium containing high concentrations of serum (e.g., >4%) to improve the efficiency of the culturing process. This maintenance period may be brief (e.g., overnight). Optionally, cells may be maintained for an extended propagation period in high-serum medium.

High-serum media for stabilization will typically contain at least 4% serum, and, in some embodiments, will contain a higher concentration of serum such as 10% or 20%. Media used for stabilization or propagation may be derived from a basal medium such as RPMI 1640, available from many commercial sources and described by Moore et al., *J Am Med Assoc* 199:519–524 (1967)). Exemplary high-serum media for maintenance or propagation include Medium 3 (RPMI 1640+10 mM HEPES, 2 mM glutamine, 5 µM ZnSO$_4$, and 10% fetal bovine serum (FBS)) and Medium 7 (RPMI 1640+10 mM HEPES, 2 mM glutamine, 5 µM ZnSO$_4$, and 20% FBS). High serum media may also be derived by mixing a particular volume of high-serum medium such as Medium 3 or Medium 7 with a particular volume of serum-free medium such as SM95, SM96, or SM98 (described herein) to arrive at a desired serum concentration (e.g., 4%–9%).

For stabilization after harvest, cells are conveniently cultured in a culture vessel at relatively high densities in a high serum medium (e.g., $10^9$ cells in 70 ml of Medium 7 (20% FBS)). However, lower cell densities and serum concentrations may be employed as well. Cells are typically maintained in the original vessel for a relatively short time (e.g., overnight) to allow for recovery from the harvesting procedure.

Following the maintenance period, cells may be transferred to low-serum media for selection and propagation of the intermediate cell population as described herein. Optionally, the cells may be cultured in a high-serum medium to allow for proliferation of the mixed cell population. In a typical embodiment, cells from the maintenance culture are reseeded into a new culture vessel containing Medium 3 (10% FBS), Medium 7 (20% FBS), or a mixture of Medium 3 and Medium 7 (15% FBS). Cells are typically cultured in this medium for 7–10 days, during which time they may grow to confluence. Once the cells have reached confluence, they may be passaged into low-serum media for selective expansion of the intermediate cell population described herein.

C. Expansion and Propagation of an Intermediate Stage Pancreatic Stem Cell Population by Culture in Low Serum Media Once the pancreatic cells have been isolated, the cells are then transferred to a selective medium to promote the emergence of a propagating intermediate stage population. This selective medium favors propagation of cells which retain the ability to secrete pancreatic endocrine hormones, or which retain the potential to mature into more differentiated cells which secrete high levels of pancreatic endocrine hormones. In general, selective medium will favor propagation of epithelial or epithelial-like cells at the expense of fibroblasts and mesenchymal cells, although pure epithelial cultures have not been shown to be required for the advantageous use of pancreatic cells in the methods of the invention. Typically, epithelial-selective media will yield a population of nearly pure (e.g., <10% fibroblasts or mesenchymal cells) cells after a certain period of growth in culture, e.g., 2, 3, 4, or 5 passages depending on the expansion of the population in each passage.

One type of selective medium which has been employed to favor epithelial cell growth from embryonic tissues is serum-free medium (see, e.g., Stephan et al., supra; Peehl and Ham, In Vitro 16:526–40 (1980)). Epithelial-specific media, and, more preferably, low-serum media containing a source of growth hormone, may be employed to select for a distinct population of propagating pancreatic cells from adult mammals that retain markers of pancreatic cell development (e.g., PDX-1), but can be further differentiated under appropriate conditions to express high levels of pancreatic endocrine hormones. Particular epithelial-selective media suitable for culture of pancreatic cells are disclosed herein, but other medium formulations known in the art to favor the preferential expansion of epithelial or epithelial-like cells may also be employed.

The transfer to epithelial-selective low-serum medium may be accomplished after a period of maintenance in high-serum medium ("weaning"), or by transferring the cells directly into selective low-serum medium following the isolation and separation procedure ("shock"). Either methodology is suitable for generation of the desired intermediate cell population.

1. Preparation of Selective Low-Serum Media

As used in this context, "low-serum medium" refers to a media having less than about 1% serum. Thus, serum-free media are a class of low-serum media. Media with a concentration of between 0% and 1% serum, e.g., about 0.1%, 0.2%, 0.3%, 0.4%, 0.5%, 0.6%. 0.7%, 0.8%, or 0.9% serum, may be prepared either by adding the appropriate concentration of serum to a serum-free medium, or by mixing serum-free and serum-containing media to achieve the desired concentration of serum.

Complete serum-free media are prepared by supplementing a basal medium (such as SM96 or 1:1 F12/DMEM) with a mixture of growth factors, other proteins, hormones and micronutrients, which substitutes for the biological functions provided by serum. An advantage of serum-free media is that the composition of the supplemental mixture may be easily manipulated to encourage the proliferation of a desired cell population (e.g., the intermediate cell population), while discouraging the growth of undesired cells (e.g., acinar cells or connective tissue cells such as fibroblasts). The supplemental mixture may also be manipulated to encourage the differentiation of a stem cell population into more mature cells, or to prevent the differentiation of a stem cell population in order to maintain high rates of proliferation.

a) Growth Hormones

Epithelial selective culture media containing growth hormone (GH) is used promote the emergence of a valuable pancreatic cell population of intermediate differentiation. Without wishing to be bound by a particular theory, it is hypothesized that GH can replace the mitogenic substances ordinarily found in serum that support cell growth, but that serum contains other mitogenic factors that promote the overgrowth of less desirable cell populations (e.g., fibroblasts and mesenchymal cells). Hence, replacement of serum with a supplemental mixture containing GH selects for propagation of a cell population with an intermediate state of differentiation. While the functions of GH in serum-free medium may be substituted with other supplemental ingredients in alternative embodiments of the invention, the ready availability of GH in natural extracts or as recombinant protein makes GH-containing media suitable epithelial-selective media for the methods disclosed herein.

Growth hormones, also known as somatotropins, are polypeptide hormones synthesized in the anterior pituitary which promote normal body growth and lactation and influence various aspects of cellular metabolism. GH has both direct effects on cells and indirect effects mediated by IGF-I and similar molecules; in the intact pancreas, islet cell growth has been connected to the expression of GH and the homologous hormones prolactin and lactogen (see, e.g., Nielsen et al., *J Mol Med* 77(1):62–6 (1999). In humans, mature GH contains 191 amino acid residues and displays a molecular mass of 22 kDa. However, in addition to the commonly observed disulfide dimer, two peptides made of portions of human GH (residues 1–43 and 44–191) have been detected in serum and have distinct effects on adult islet tissue (see Lewis et al, *Endocr J* 47 Suppl:S1–8 (2000)). Various naturally occurring derivatives, variants, metabolic products, and engineered derivatives of human GH are known, including glycosylated GH, methionyl GH, 20 kDa GH, acetylated GH, proteolytically cleaved GH, desamido GH, sulfoxide GH, and truncated forms of GH.

GH is a member of a conserved family of hormones including, in humans, GH-V1 and GH-V2, choriomammotropin and prolactin and proteins from other vertebrates such as rodent placental lactogens I and II and other bovine and sheep lactogens, murine proliferin I, II, and III and proliferin-related protein, bovine prolactin-related proteins I, II, and III, rat prolactin-like proteins A and B, and somatolactins from various fishes. Members of this family are characterized by the consensus sequences C-x-[ST]-x (2)-[LIVMFY]-x-[LIVMSTA]-P-x(5)-[TALIV]-x(7)-[LIVMFY]-x(6)-[LIVMFY]-x(2)-[STA]-W or C-[LIVMFY]-x(2)-D-[LIVMFYSTA]-x(5)-[LIVMFY]-x (2)-[LIVMFYT]-x(2)-C.

Growth hormone suitable for practice of the invention may obtained from a variety of natural and artificial sources. In contrast to therapeutic uses of GH, which often require GH of the same species, GH from a range of primate, mammalian, or vertebrate species may be employed in formulation of low-serum media for culture of pancreatic cells. A convenient source of growth hormone is bovine pituitary extract (BPE), which is a rich source of natural GH. BPE (75 µg/ml protein) may be included in the culture medium at about 0.1 to 100 µl/ml, preferably at 0.5 to 50 µl/ml, and most preferably at 5 µl/ml or 37.5 mg/l. Pituitary extracts available from other species (e.g., porcine, ovine, and the like) may also be employed at similar concentrations. Other factors present in pituitary extract may potentiate its effect, but satisfactory results may also be achieved with purified GH, and with recombinant GH. Recombinant bovine and human GH are widely available and are a suitable source of GH activity. Recombinant GH may be added to culture medium at between 0.01 and 100 mg/l, preferably between 0.1 and 10 mg/l, more preferably at about 0.2, 0.5, 0.75, 1, 1.25, 2, or 5 mg/l, and most preferably at about 1.25 mg/L, where 1 mg of recombinant protein is about equivalent to 3 IU of GH.

b) Other Supplements

Typical ingredients added to basal media for complete serum-free media include recombinant human insulin (0.1 to 100 µg/ml), transferrin (0.1 to 100 µg/ml), epidermal growth factor (0.1 to 100 ng/ml), ethanolamine (0.1 to 100 µg/ml), aprotinin (0.1 to 100 µg/ml), glucose (0.1 to 100 mg/ml), phosphoethanolamine (0.1 to 100 µM), triiodothyronone (0.1 to 100 µM), selenium (0.1 to 100 nM), hydrocortisone (0.01 to 100 µM), progesterone (0.1 to 10 nM), forskolin (0.1 to 100 µM), heregulin (0.1 to 100 nM), and bovine pituitary extract (0.1 to 500 µg/ml). Not all supplemental ingredients are required to support cell growth; the optimal concentration or necessity for a particular supplement may be determined empirically, by leaving out or reducing the concentration of a single ingredient and observing the effect on cell proliferation (see Stephan et al., supra).

In general, supplemental ingredients may be replaced by natural or synthetic products having the same biological properties. For example, triiodothyronone, hydrocortisone, and progesterone may all be replaced by natural or synthetic hormones known to activate the same intracellular receptors (thyroid receptors, glucocorticoid receptors, and progesterone receptors). Insulin and EGF are typically human proteins produced by recombinant DNA methodology, but may be replaced by polypeptides purified from natural sources, by polypeptides from other species, or by other agonists of the insulin and EGF receptors. GH may, in some cases, be substituted with other antagonists of the GH receptor. Likewise, heregulin, a ligand of the ErbB3 receptor, may be replaced by heregulin isoforms and other ErbB3 agonists such as NRG2, NRG3, and NRG4, sensory and motor neuron-derived factor, neurestin, and Ebp-1, heregulin α, heregulin β, heregulin γ, neuregulin-1 and neuregulin-2 (NRG-1 alpha, NRG-1 beta, NRG-2 alpha, and NRG-2 beta.

Exemplary serum-free media include the basal medium SM96 and the complete medium SM95, which consists of SM96 supplemented as shown in the following tables. SM98 consists of 1:1 F12/DMEM supplemented with a modification of medium supplement 14F described by Stephan et al., supra. SM98 contains less heregulin (1 ng/ml v. 8 ng/ml) than 14F. Thus, SM 98 consists of 1:1 F12/DMEM supplemented with recombinant human insulin, 10 µg/ml; transferrin, 10 µg/ml; epidermal growth factor, 10 ng/ml; ethanolamine, 61 ng/ml; aprotinin, 25 µg/ml; glucose, 5 mg/ml; phosphoethanolamine, 141 ng/ml; triiodothyronone, 3.365 pg/ml; selenium, 4.325 ng/ml; hydrocortisone, 181 ng/ml; progesterone, 3.15 ng/ml; forskolin, 410 ng/ml; heregulin, 1 ng/ml; and bovine pituitary extract, 75 µg/ml. Exemplary sources of EGH and heregulin in SM95 and SM98 are recombinant human EGF (Sigma E9644) and the EGF domain (amino acids 176–246) of human heregulin-β1 (R&D systems 396-HB/CF).

| RPMI 1640 Media | |
|---|---|
| | Mg/L |
| (Moore, et al., A.M.A., 199:519 (1967)) | |
| INORGANIC SALTS | |
| Ca(NO$_3$)$_2$-4H$_2$O | 100 |
| KCl | 400.00 |
| MgSO$_4$ (anhyd.) | 48.84 |
| NaCl | 5850.00 |
| Na$_2$HPO$_4$ (anhyd.) | 800.00 |
| OTHER COMPONENTS | |
| D-Glucose | 2000.00 |
| Glutathione (reduced) | 1.0 |
| HEPES | 5958.00 |
| Phenol Red | 5.00 |
| AMINO ACIDS | |
| L-Arginine | 200.00 |
| L-Asparagine (free base) | 50.00 |
| L-Aspartic Acid | 20.00 |
| L-Cystine.2HCl | 65.00 |
| L-Glutamic Acid | 20.00 |
| L-Glutamine | 300.00 |
| Glycine | 10.00 |
| L-Histidine (free base) | 15.00 |
| L-Isoleucine | 50.00 |
| L-Leucine | 50.00 |
| L-Lysine.HCl | 40.00 |
| L-Methionine | 15.00 |
| L-Phenylalanine | 15.00 |
| L-Proline | 20.00 |
| L-Serine | 30.00 |
| L-Threonine | 20.00 |
| L-Tryptophan | 5.00 |
| L-Tyrosine.2Na$_2$H$_2$O | 29.00 |
| L-Valine | 20.00 |
| VITAMINS | |
| Biotin | 0.20 |
| D-Ca Pantothenate | 0.25 |
| Choline Chloride | 3.00 |
| Folic Acid | 1.00 |
| i-Inositol | 35.00 |
| Niacinamide | 1.00 |
| Pyridoxine.HCl | 1.00 |
| Riboflavin | 0.20 |
| Thiamine.HCl | 1.00 |
| Thymidine | 0.005 |
| Vitamin B$_{12}$ | 1.04 |

-continued

RPMI 1640 Media

| | Mg/L |
|---|---|
| SM95 | |
| INORGANIC SALTS | |
| $CaCl_2$ | 78.3 |
| $CuSO_4.5H_2O$ | 0.00165 |
| $Fe(NO_3)_3.9H_2O$ | 0.025 |
| $FeSO_4.7H_2O$ | 0.61 |
| KCl | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4.H_2O$ | 31.25 |
| $ZnSO_4.7H_2O$ | 0.416 |
| AMINO ACIDS | |
| L-Alanine | 11.225 |
| L-Arginine.HCl | 283.75 |
| L-Asparagine.$H_2O$ | 18.75 |
| L-Aspartic Acid | 16.325 |
| L-Cysteine.$H_2O$ (non-animal) | 43.78 |
| L-Cystine.2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl.$H_2O$ | 38.69 |
| L-Isoleucine | 31.24 |
| L-Leucine | 42.5 |
| L-Lysine.HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine.2$Na_2H_2O$ (non-animal) | 35.9 |
| L-Valine | 38.125 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine.2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| L-Inositol | 24.3 |
| Niacinamide | 1.03 |
| Pyridoxine.HCl | 1.046 |
| Riboflavin | 0.13 |
| Thiamine.HCl | 1.23 |
| Thymidine | 0.5325 |
| Vitamin $B_{12}$ | 1.04 |
| SUPPLEMENTS | |
| Na Selenous Acid | 0.0034 |
| Epithelial Growth Factor | 0.005 |
| Ethanolamine | 0.03 |
| Phosphoethanolamine | 0.07 |
| Aprotinin | 12.5 |
| Progesterone | 0.0016 |
| Forskolin | 0.205 |
| HeregulinB | 0.004 |

-continued

RPMI 1640 Media

| | Mg/L |
|---|---|
| Bovine Pituitary Extract | 37.5 |
| Hydrocortisone | 0.0923 |
| r.h. insulin | 5.05 |
| $T_3$ | 0.0000015 |
| L-Thyroxine Na | 0.00002 |
| Bovine Transferrin APG | 7.5 |
| SM96 | |
| INORGANIC SALTS | |
| $CaCl_2$ | 78.3 |
| $CuSO_4.5H_2O$ | 0.00165 |
| $Fe(NO_3)_3.9H_2O$ | 0.025 |
| $FeSO_4.7H_2O$ | 0.61 |
| KCl | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4.H_2O$ | 31.25 |
| $ZnSO_4.7H_2O$ | 0.416 |
| AMINO ACIDS | |
| L-Alanine | 11.225 |
| L-Arginine.HCl | 283.75 |
| L-Asparagine.$H_2O$ | 18.75 |
| L-Aspartic Acid | 16.325 |
| L-Cysteine.$H_2O$ (non-animal) | 43.78 |
| L-Cystine.2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl.$H_2O$ | 38.69 |
| L-Isoleucine | 31.24 |
| L-Leucine | 42.5 |
| L-Lysine.HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine.2$Na_2H_2O$ (non-animal) | 35.9 |
| L-Valine | 38.1261 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine.2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| i-Inositol | 24.3 |
| Niacinamide | 1.03 |
| Pyridoxine.HCl | 1.046 |
| Riboflavin | 0.13 |
| Thiamine.HCl | 1.23 |
| Thymidine | 0.6325 |
| Vitamin $B_{12}$ | 1.04 |

2. Transfer of Cells to Low-Serum Media

Transferring a culture of pancreatic cells to low-serum media promotes the selection of a defined population of cells with an intermediate state of differentiation. This cell population will continue to proliferate if subcultured, but maintains high expression levels of pancreatic markers such as PDX-1. Unstimulated, this population secretes relatively low levels of pancreatic endocrine hormones such as insulin, but can be matured according to the methods of the invention to yield high-secreting cells. To transfer a culture of pancreatic cells to low-serum medium, the cells may be weaned from high-serum to low-serum media, or may be placed directly in low-serum media following isolation. Medium such as SM95 and SM98 are suitable low-serum media, although SM95 yields slightly improved insulin secretion upon maturation of the of pancreatic cells.

The intermediate cell population typically retains both the ability to proliferate and the ability for further differentiation into high-secreting endocrine cells. Proliferative ability is generally assessed by the ability of a culture seeded at a one density to expand to a second density; e.g., cells plated at 180 cells per square centimeter may be expanded to 1,800 cells per ml in a single passage. By repeated cycles of propagation and passage, a starting population of isolated pancreatic cells may be expanded by about 10,000-fold or more (e.g., about 100-fold, 500-fold, 1000-fold, 5000-fold, 10,000-fold, 50,000-fold, 100,000-fold, 500,000-fold, or 1,000,000 fold) while retaining endocrine markers such as PDX-1 and insulin mRNA expression, and retaining the ability to differentiate into mature high-secreting endocrine cells.

III. Adaptive Cell Culture

As a preliminary step in the maturation process, intermediate stage pancreatic stem cells are grown under adaptive culture conditions Briefly, the intermediate stage pancreatic stem cells are grown on conditioned culture dishes or new culture dishes, while care is taken to ensure the cells do not reach confluence. Cells from both types of dishes are combined and are either encapsulated as described below, or reseeded onto culture dishes.

A. Conditioned Culture Plates

Conditioned culture dishes are culture dishes that have been used previously to grow intermediate stage pancreatic stem cells. Once the cells have formed a monolayer (typically about 5 days, depending on the initial subculture seeding density), they are removed by trypsinization. Growth of a 100% confluent cell culture is not required to produce a conditioned culture dish. A lowered concentration of trypsin (typically ½ or ¼ of the concentration employed in standard cell culture techniques) is preferred to prevent extensive degradation of the matrix. Alternatively, the cell monolayer may be removed by extracting the substrate with detergent, which will remove the cells but leave behind the secreted matrix (see Gospodarowicz et al., *Proc Natl Acad Sci USA* 77:4094–8 (1980)).

Conveniently, the removed cells which previously grew on the substrate or culture dish may be split and reseeded on the same, now conditioned, culture dish. However, the culture which conditions the substrate and the culture which is seeded on the substrate need not be the same culture. Accordingly, one culture of cells may be grown on a substrate to condition the substrate, the cells removed, and cells from another culture seeded upon the conditioned substrate. The conditioning cells may be from the same or different donor or species as the cells subsequently cultured.

B. Growth of Cells Using Adaptive Culture

Intermediate stage pancreatic stem cells are split onto a mixture of conditioned and new culture dishes. The amount of time in culture is not critical so long as the cells are still capable of proliferation. In a preferred embodiment, cells that have been recently isolated from pancreas (e.g. passaged only once or twice) are used. As before, to promote growth of the intermediate stage pancreatic stem cells population, the cells are grown in low serum media. Cells are seeded at a density such that they do not touch each other and are preferably harvested before reaching confluence. One of skill in the art will recognize that the number of cells seeded will affect the amount of time in culture before confluence is reached.

After harvest the cells from conditioned and new plates are combined. The ratio of cells grown on new plates to cells grown on conditioned plates is not critical to the invention, so long as some cells are grown on conditioned plates.

The harvested cells can then be encapsulated as described below, or seeded onto new tissue culture plates. Cells that have undergone adaptive culture and are then grown in culture are able to both proliferate and secrete high levels of insulin in a glucose regulated manner. Insulin to actin ratios are similar to those before adaptive culture.

IV. Encapsulation of Intermediate Proliferating Pancreatic Cells

Encapsulation of the intermediate proliferating stem cells after adaptive culture results in the formation of cellular aggregates in the capsules. The aggregates have cellular architecture and protein expression phenotypes similar to those of encapsulated islets freshly isolated from pancreas.

Encapsulation can also allow the pancreatic cells to be transplanted into a diabetic host, while minimizing the immune response of the host animal. The porosity of the encapsulation membrane can be selected to allow secretion of biomaterials, like insulin, from the capsule, while limiting access of the host's immune system to the foreign cells.

Encapsulation methods are known in the art and are disclosed in the following references: van Schelfgaarde & de Vos, *J. Mol. Med.* 77:199–205 (1999), Uludag et al. *Adv. Drug Del Rev.* 42:29–64 (2000) and U.S. Pat. Nos. 5,762,959, 5,550,178, and 5,578,314. Below is a general description of encapsulation of intermediate stage pancreatic stem cells. A specific example is found in the Example section of this application.

A. Encapsulation Materials

Encapsulated cells are surrounded by a hydrogel. Hydrogels can be made from a variety of materials including alginate, agarose, and polyethylene glycol (PEG). These materials form hydrogels in water when cross-linked, either ionically or covalently.

A preferred material for use in encapsulating pancreatic cells is alginate, a polysaccharide composed of mannuronic (M) acid and guluronic (G) acids. Alginate forms a hydrogel when cross linked with a divalent cation, such as calcium or barium.

B. Capsule Formation

As an example of encapsulation of cells, formation of alginate capsules with polylysine membranes is described. Those of skill in the art will recognize that capsules can also be formed using varients of alginate and polylysine or other materials and that the formation process can similarly be modified without affecting the function of the encapsulated cells. Assays to test the function of the cells are provided in this application at section IV on Implantation of encapsulated cells and section VI on phenotypic assays.

Droplets containing cells and alginate are made in a droplet forming device, such as an air driven droplet generator or a high voltage electrostatic pulse system. Droplets can also be made using gravity. The alginate solution is formed into a gel by incubating the droplet in a solution containing an ionic cross-linker such as calcium.

To form a membrane, the polyanionic alginate is coated with polycationic polysine, by suspending the droplet in a solution containing polylysine. Those of skill in the art will recognize that varying the molecular weight and concentration of the polylysine, as well as the incubation time, will affect the porosity of the membrane.

Once the membrane has been formed around the hydrogel, the user has the option of liquefying the gel by removing calcium ions, usually by soaking the capsules in a solution of sodium citrate. Those of skill in the art will recognize situations where liquefaction is appropriate. A final step to promote biocompatability is to suspend the capsules in alginate or some other charged molecule to bind the positively charged polylysine.

C. Incorporation of Microcapsules into Macrocapsules

Those of skill in the art will recognize that in some situations additional steps can be taken to reduce host responses to implanted encapsulated pancreatic cells. A preferred method is to incorporate microcapsules into a macrocapsule. The technique is described in U.S. Pat. No. 5,545,423 herein incorporated by reference.

Briefly, microcapsules are made essentially as described in the previous section. Although microcapsules with a liquefied interior can be used, microcapsules with a gelled interior are preferred. A plurality of microcapsules are then covered with a thick layer of gelled material, with the result that the polycation layer of the microcapsule is more effectively masked from the immune system.

The macrocapsule layer covering the microcapsules can be any thickness, but is at least about 1 micron thick and preferably about at least 50 microns thick. The macrocapsule can be made of any polymer suitable for making a hydrogel as described for microcapsules and can be cross-linked using ionic or covalent methods. Macrocapsules can be made in a variety of shapes, including but not limited to cylinders, spheres, or discs. Those of skill in the art will recognize that the particular composition of the macrocapsule will not affect the function of the encapsulated cells, and furthermore will be able to assay for the function of the encapsulated cells using the teaching of this application.

D. Aggregation of Encapsulated Cells and Their Maintenance in Culture

After encapsulation the intermediate proliferating stem cells form aggregates. The cellular architecture and protein expression patterns of the aggregates can be analyzed by immunostaining as described in section VI of this application. A typical aggregate of cells has the following phenotype: a single layer of cells surrounds the periphery of the aggregate and expresses CK-19, while cells on the interior of the aggregate express insulin, somatostatin, and glucagon. The CK-19 expressing cells are likely undifferentiated cells; the hormone expressing cells at the center are likely mature cells.

Encapsulated cells can be grown in culture as can encapsulated islets. Thus, encapsulated intermediate proliferating stem cells can maintained in culture in a manner similar to that used for encapsulated islets. Divalent cation may be added to the culture media to maintain the liquid state. For example, 0.03 mM $CaCl_2.2H_2O$ can be added to the culture media when the hydrogel is alginate crosslinked with calcium.

V. Implantation of Encapsulated Pancreatic Cells

Implantation or transplantation into a mammal and subsequent monitoring of endocrine function may be carried out according to methods commonly employed for islet transplantation; see, e.g., Ryan et al., *Diabetes* 50:710–19 (2001); Peck et al., *Ann Med* 33:186–92 (2001); Shapiro et al., *N Engl J Med* 343(4):230–8 (2000); Carlsson et al., *Ups Med Sci* 105(2):107–23 (2000) and Kuhtreiber, WM, Cell Encapsulation Technology and Therapeutics, Birkhauser, Boston, 1999. Preferred sites of implantation include the peritoneal cavity, the liver, and the kidney capsule.

A. Dosage of Microcapsules

One of skill in the art will be able to determine an appropriate dosage of microcapsules for an intended recipient. The dosage will depend on the insulin requirements of the recipient. Insulin levels secreted by the microcapsules can be determined immunologically or by amount of biological activity. The recipients body weight can also be taken into account when determining the dosage. If necessary, more than one implantation can be performed as the recipient's response to the encapsulated cells is monitored. Thus, the response to implantation can be used as a guide for the dosage of encapsulated cells. (Ryan et al., *Diabetes* 50:710–19 (2001))

B. Monitoring Encapsulated Cell Function in an Animal.

The function of encapsulated cells in a recipient can be determined by monitoring the response of the recipient to glucose. Implantation of the encapsulated cells can result in control of blood glucose levels. In addition, evidence of increased levels of pancreatic endocrine hormones, insulin, glucagon, and somatostatin can indicate function of the transplanted encapsulated cells.

One of skill in the art will recognize that control of blood glucose can be monitored in different ways. For example, blood glucose can be measured directly, as can body weight and insulin requirements. Oral glucose tolerance tests can also be given. Renal function can also be determined as can metabolic parameters. (Soon-Shiong, P. et al., *PNAS USA* 90:5843–5847 (1993); Soon-Shiong, P. et al., *Lancet* 343: 950–951 (1994)).

VI. Phenotypic Assays

To know when mature pancreatic cells are present, it is useful to assay the phenotypes of pancreatic cells at particular stages of culture and after encapsulation, whether grown in vivo or in vitro. Since expression of particular proteins correlates with cell identity or differentiation state, cells may be analyzed for the expression of a marker gene or protein to assess their identity or differentiation state. For example, in freshly isolated pancreatic tissue, expression of amylase identifies the cell as an exocrine acinar cell, while expression of insulin identifies the cell as an endocrine islet cell. Likewise, islet cells at an early stage of differentiation are usually positive for the cytokeratin CK-19, while mature islet cells show less expression of CK-19.

Phenotypic properties may be assayed on a cell-by-cell basis or as a population average. The mode of assay will depend on the particular requirements and methodology of the assay technique. Thus, assays of marker expression by immunohistochemistry, performed on fixed sections or on suspended cells by FACS analysis, measure the frequency and intensity with which individual cells express a given marker. On the other hand, it may be desirable to measure properties such as the average insulin to actin mRNA expression ratio over an entire population of cells. In such cases, the assay is typically performed by collecting mRNA from a pool of cells and measuring the total abundance of insulin and actin messages. Many phenotypic properties may be assayed either on a cell or population basis. For example, insulin expression may be assayed either by staining individual cells for the presence of insulin in secretory granules, or by lysing a pool of cells and assaying for total insulin protein. Similarly, mRNA abundance may be measured over a population of cells by lysing the cells and collecting the mRNA, or on an individual cell basis by in situ hybridization.

A. Cell Differentiation Markers

There are a number of cellular markers that can be used to identify populations of pancreatic cells. Donor cells isolated and cultured begin to display various phenotypic and genotypic indicia of differentiated pancreatic cells. It is believed that the changes in these indicia or markers are a response to the shift of the pancreatic cells to a serum-free environment, whether after an initial proliferation phase or immediately after isolation and purification. Examples of the phenotypic and genotypic indicia include various molecular markers present in the facultative progenitor cell population that are modulated (e.g., either up or down regulated). These molecular markers include CK-19, which is hypothesized to be a marker of the pancreatic facultative stem cell.

Typically, mammalian stem cells proceed through a number of developmental stages as they mature to their ultimate developmental endpoint. Developmental stages often can be determined by identifying markers present or absent in developing cells. Because human endocrine cells develop in a similar manner, various markers can be used to identify cells as they transition from a stem cell-like phenotype to pseudoislet phenotype.

The expression of markers in cells induced to proliferate or differentiate by the methods of the present invention bears some similarity to the sequence of marker expression in normal human pancreas development. Very early in development, the primordial epithelial cells express PDX-1, an early cellular marker that is a homeodomain nuclear factor. As the cells develop, they begin to bud out and form a duct. These cells express cytokeratin 19, a marker for epithelial ductal cells, and temporally express PDX-1 leading developmentally to endocrine cells. As these cells continue to develop, they gain the ability to express insulin, somatostatin, or glucagon. The final differentiated cells are only able to express one and become the α cells (glucagon), β cells (insulin), and δ cells (somatostatin). The intermediate cell population used herein is believed to be at a less than fully differentiated stage of development, retaining the ability to proliferate and the potential to differentiate into mature endocrine cells. Whether the cells are indeed examples of a precursor in the development pathway or simply a result of in vitro manipulation, the intermediate stage cells are able to proliferate as well as to express endocrine hormones and, therefore, have the potential for being used to correct a deficiency in any type of islet cell.

Markers of interest are molecules that are expressed in temporal- and tissue-specific patterns in the pancreas (see Hollingsworth, *Ann N Y Acad Sci* 880:38–49 (1999)). These molecular markers are divided into three general categories: transcription factors, notch pathway markers, and intermediate filament markers. Examples of transcription factor markers include PDX-1, NeuroD, Nkx-6.1, Isl-1, Pax-6, Pax-4, Ngn-3, and HES-1. Examples of notch pathway markers include Notch1, Notch2, Notch3, Notch4, Jagged1, Jagged2, Dll1, and RBPjk. Examples of intermediate filament markers include ck19 and Nestin.

Methods for assessing expression of protein and nucleic acid markers in cultured or isolated cells are standard in the art and include quantitative reverse transcriptase polymerase chain reaction (RT-PCR), Northern blots, and in situ hybridization (see, e.g., *Current Protocols in Molecular Biology* Ausubel et al., eds. 2001 supplement)) and immunoassays, such as immunohistochemical analysis of sectioned material, Western blotting, and, for markers that are accessible in intact cells, flow cytometry analysis (FACS) (see, e.g., Harlow and Lane, *Using Antibodies: A Laboratory Manual*, New York: Cold Spring Harbor Laboratory Press (1998)). Conventional histochemical markers of endocrine cell differentiation may also be employed. Cells to be examined by immunohistochemistry may be cultured on glass chamber slides for microscopic examination. Alternatively, cells grown in conventional tissue culture may be manually removed from the culture and embedded in paraffin for sectioning. PDX-1 antibody can be made following the teachings of Leonard J. et al., Mol. Endocrinol., Oct. 7, 1993 (10) 1275–83.

Cell differentiation markers are varied and can be detected by conventional immunohistochemistry. A generally applicable protocol follows.

The staining process begins with removing chamber portion of the slides. Cells were very gently rinsed with in buffers and fixed in paraformaldehyde solution. Cells are then incubated in a blocking solution containing normal serum at room temperature. Cells were permeabilized with non-ionic detergent in blocking solution. Primary antibodies as listed below are prepared in blocking solution at appropriate dilution and added to cells and incubated. Following incubating with primary antibody, cells were rinsed in buffer and reblocked in blocking solution.

Secondary antibody prepared in blocking solution at appropriate dilution is added to the cells and incubated in the dark. Following incubation the cells are rinsed and nuclei were counterstained with Hoechst dye. Excess fluid is removed and the slides are mounted and covered with coverslides. The slides dry and are stored in the dark.

Alternatively the cells can be prepared for immunocytochemistry using the ABC method. In brief, the cells are embedded in parafin and slides with paraffin sections are dried at 37° C. overnight. The cells are deparaffinized and immersed in a hydrogen peroxide methanol solution to inhibit endogenous peroxidase activity. Slides were boiled in 0.01 citrate buffer (pH 6.0) for 30 minutes to recover certain epitopes. Slides were rinsed with buffer and blocked using normal serum at room temperature in a moist chamber.

Primary antibody prepared in blocking solution are added to the samples and incubated in a moist chamber. Slides are washed and incubated with secondary antibody prepared in blocking solution. Slides were again rinsed with buffer and incubated with Avidin-Horse Reddish Peroxides reagent or ABC complex from a commercial kit (e.g. Dako Corporation). Slides are again rinsed and incubated with diaminobenzidin developing solution; urea hydrogen peroxides in a gold wrap. After washes with distilled water, slides are immersed in Mayer's Hematoxylin for 5 minutes, then kept slides in running tap water until water turned colorless and nuclei were blue. Slides are dehydrated and mounted for viewing.

B. Insulin mRNA Expression

One marker that may be used to characterize pancreatic cell identity, differentiation, or maturity is the level of insulin mRNA. For example, the intermediate cell population of the present invention show expression of insulin mRNA within a defined range. Method for quantitating insulin mRNA include Northern blots, nuclease protection, and primer extension. In one embodiment, RNA is extracted from a population of cultured cells, and the amount of proinsulin message is measured by quantitative reverse transcription PCR. Following reverse transcription, insulin cDNA is specifically and quantitatively amplified from the sample using primers hybridizing to the insulin cDNA sequence, and amplification conditions under which the amount of amplified product is related to the amount of mRNA present in the sample (see, e.g., Zhou et al., J Biol Chem 272:25648–51 (1997)). Kinetic quantification procedures are preferred due to the accuracy with which starting mRNA levels can be determined.

Frequently, the amount of insulin mRNA is normalized to a constitutively expressed mRNA such as actin, which is specifically amplified from the same RNA sample using actin-specific primers. Thus, the level of expression of insulin mRNA may be reported as the ratio of insulin mRNA amplification products to actin mRNA amplification products, or simply the insulin:actin mRNA ratio. The expression of mRNAs encoding other pancreatic hormones (e.g., somatostatin or glucagon) may be quantitated by the same method.

C. Glucose-Stimulated Insulin Secretion

One of the important functions of a beta cell is to adjust its insulin secretion according to the glucose level. Typically, a static glucose stimulation (SGS) assay may be performed on the proliferating adherent pancreatic cells to identify whether they are able to secrete insulin in response to different glucose levels. Cells are generally cultured on an appropriate substrate until nearly confluent. Three days prior to the SGS test, the culture medium is replaced by a medium of similar character but lacking insulin and containing only 1 g/L of glucose. The medium is changed each day for three days and the SGS test is performed on day four.

Before the test, the culture medium may be collected for glucose and insulin analysis. To prepare cells for the test, cells are washed twice with Dulbecco's phosphate-buffered saline (DPBS)+0.5% BSA, incubating for 5 minutes with each wash, and then once with DPBS alone, also incubating for 5 minutes. After washing, the cells are incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation is then repeated.

To perform the SGS assays, cells are incubated in 3 ml (100 mm dish) or 4 ml (T75 flask) or 2 ml (60 mm dish) KRB-60, at 37° C. for 20 minutes. The medium is aspirated and spun, and is collected for insulin assay as LG-1 (low glucose stimulated step). KRB-450+theo (KRB with 450 mg/dl glucose and 10 mM theophylline) is then added with the same volume as above, and cells are cultured under the same condition as above. The supernatant is collected for insulin assay as HG (high glucose stimulated). The cells are then incubated again with KRB-60 and the medium collected as LG-2, and another time as LG-3. The media are collected for insulin analysis, and stored at −20° C. until insulin content is determined by radioimmunoassay (RIA) or other suitable assay.

The results of the SGS test are often expressed as a stimulation index, defined as the HG insulin value divided by the LG-1 insulin value. Generally, a stimulation index of about 2 or greater is considered to be a positive result in the SGS assay, although other values (e.g., 1.5, 2.5, 3.0, 3.5, etc.) may be used to define particular cell populations.

EXAMPLES

The following examples are offered to illustrate, but not to limit the claimed invention.

Example 1

Generation of a Population of Intermediate Stage Pancreatic Stem Cells for in situ Maturation Typically, the intermediate stage pancreatic stem cells are isolated from donor pancreas. A mixed population of isolated pancreatic cells is cultured under conditions to promote the growth of the intermediate stage pancreatic stem cells.

Organ Procurement

The pancreatic cells were isolated from cadaver pancreas. The pancreas was retrieved from a multi-organ donor, a 59-year-old male Caucasian. Organ harvesting was orchestrated by United Network for Organ Sharing (UNOS) and local organ donor organizations.

To remove the pancreas, the abdominal aorta was first cannulated below the junction of renal artery. Portal perfusion was done via cannulation of the inferior mesenteric vein. The cannula was inserted up to and above the junction of the portal vein and the splenic vein. A 2-0 tie was put around the splenic vein at the junction of the portal vein. Another 2-0 tie was put around the splenic artery.

The splenic vein was ligated and cut open on the spleen side immediately before the perfusion was started. This method makes pancreatic perfusion more efficient without building up high pressure, which can damage the islets. It also avoids draining the perfusant from spleen and pancreas into the liver. The lesser sac was opened and normal saline slush was applied to pancreas. After one liter of Aortic perfusion, the splenic artery was ligated.

The pancreas was well-protected when the liver and kidney teams dissected the splenic vein and lower gastric vessels. The pancreas was divided at the edge of duodenum, reducing the risk of damage to the pancreas and also reducing the risk of contamination.

The organ was stored in plastic bag filled with UW solution and set in a Nalgene jar with sterile normal saline slush for transportation.

Isolation of Human Islets from Donor Pancreas

Pancreatic tissue was dissociated by mechanical disruption and digestion with Liberase in HBSS (1.5 mg/ml). Two hundred and forty milliliters of Liberase solution was infused into the pancreas via ductal cannulation. The organ was incubated in an 800 ml tempering beaker, at 37° C. until the tissue became soft, about 10 to 20 minutes.

The main duct was removed from the tissue mass which was then transferred into a metal digestion chamber; automatic circulating digestion was started. When free islets appeared in the sample, 200 ml digestant was collected and 120 ml (0.75 mg/ml) fresh Liberase solution was added into the system for further digestion.

After the majority of islets were released from the surrounding tissue the digestant was collected and diluted with Medium A10 (10% FBS in RPMI). The cells were washed with A10 three times, by centrifugation at 4° C. 1,000 rpm, for two minutes.

Islets were separated from acinar cells by a three-layer density gradient separation in a solution of PIPS (Nycodenz (Nycomed AS, Norway) in UW solution) as described in U.S. Pat. No. 5,739,033.

The pellet of washed pancreatic cells was mixed with 320 ml PIPS (density 1.114) and incubated on ice for 10 minutes. Eight 250 ml flat-bottom centrifuge tubes were filled with 70 ml PIPS (density 1.090). Forty milliliters of cell/PIPS suspension was under-laid into each tube. Sixty milliliters of RPMI with 2% FBS was over-laid on top of the PIPS. Tubes were centrifuged using a Sorvall RC-3C Plus with a 05, ARC rotor at 1,500 rpm, for six minutes without braking.

The upper interface (413,400 IEQ, 67% purity), lower interface (mixture of entrapped islets, fragmental islets, acinar and ductal cells) and the pellet (mainly acinar and ductal cells) were collected separately.

Cells were washed two more times with Medium A10 and then used for either clinical transplantation (75%) or proliferation studies (25%).

Preferential Culture of Intermediate Stage Pancreatic Stem Cells

Following islet isolation, a cell fraction containing approximately 57% islets was immediately placed in tissue culture dishes for proliferation. The initial culture was referred to as passage 0 (p0) cells. Initially, cells were grown in a mixed medium composed of 87% of serum free SM 95 and 13% Medium #7 with 20% FCS. Medium compositions are listed at section IIIA2 of this application. At the first medium change on day 4, the p0 cells were switched to 100% serum free SM95 medium. The culture medium was changed twice a week throughout the culture period and floating cells were removed with spent medium.

After twelve days in culture, the p0 cells reached confluence. The cells were dissociated from the bottom of the culture dishes with trypsin/EDTA for about ten minutes, and then washed with 10% FBS HBSS medium. P0 cells were subcultured with a one to two split into new tissue culture dishes, becoming passage 1 (p1) cells. At this and subsequent cell passages, cells were seeded at a density of about 12,000 cells per centimeter squared of culture surface.

Example 2

Adaptive Culture of Intermediate Stage Pancreatic Stem Cells

As a preliminary step to maturation, intermediate stage pancreatic stem cells are grown on a combination of conditioned culture dishes and new culture dishes.

P1 Cells were cultured for seven days and then subcultured, becoming passage 2 (p2) cells. About ⅔ of the harvested cells from p1 were seeded into conditioned cell culture dishes. The conditioned cell culture dishes had previously been used for culturing pancreatic cells from another donor, HD 386i. The remaining ⅓ of the cells were seeded into new, non-conditioned tissue culture dishes. Cells on both conditioned plates and new plates continued to proliferate P2 cells were cultured for seven days. The estimated cell expansion of passages 1 and 2 combined was approximately 10-fold. Cells from new and conditioned dishes were harvested and combined. A portion of these proliferated cells were seeded into new tissue culture dishes becoming cultured passage 3 (p3) cells. Another portion of the cells was encapsulated in alginate-polylysine microcapsules referred to as encapsulated p3 cells.

Example 3

Characterization of p3 Cells Grown in Culture without Encapsulation

The p3 cells were seeded onto new plates and grown in serum free SM95 media under standard culture conditions. In vitro analysis of the cells showed stable levels of insulin and glucagon mRNA were expressed, as compared to p1 and p2 cells. However, the P3 cells in culture secreted high levels of insulin in a glucose regulated manner suggesting the P3 cells had normal islet-like function.

Assay of Insulin and Glucagon mRNA Levels

Insulin and glucagon mRNA expression from cultured p0, p2, and p3 cells was determined by RT-PCR assay. RNA was isolated using the RNeasy mini kit (QIAGEN #74104) according to the manufacturer's instructions. Briefly, lysis buffer (650 μl per 10 cm plate) was added to the cells, collected with a disposable cell scraper (Fisher #087732), and then disrupted with a QIAshredder (QIAGEN #79654). Total RNA was isolated from the lysate, and then quantitated using the RiboGreen RNA Quantitation assay (Molecular Probes #R-11490). The RNA sample was stored frozen at −80° C. until cDNA synthesis. Duplicate aliquots (0.5 μg each) of each sample was reverse transcribed with the Omniscript RT kit (QIAGEN #205111) according to the manufacturer's instructions using 20 pmoles of oligo-$(dT)_{16}$, and then each cDNA sample was diluted to 100 μl with TE buffer pH8.0 and stored at −20° C. Real-time PCR was performed on a Roche Molecular LightCycler using 2 μl of each cDNA sample and the indicated primers. Actin and insulin were measured with a hybrid probe protocol and DNA Master Hybridization mix (Roche #2158825) according to the manufacturer's instructions. PCR was quantitated by comparison with a standard curve of each product amplified in parallel.

|  | sense | antisense | FITC probe | LC RED probe |
|---|---|---|---|---|
| Beta-actin | CCTCGCCTTTGCCG ATCC (SEQ ID NO:1) | AGCCACACGCAGCT CATTGTAGA (SEQ ID NO:3) | CCCATCGAGCACGG CATCGTCACCAA (SEQ ID NO:5) | TGGGACGACATGGA GAAAATCTGGCACCAC (SEQ ID NO:7) |
| Insulin | GCCATCAAGCACAT CACTGT (SEQ ID NO:2) | AGAGGCACCAGATG CTGGTA (SEQ ID NO:4) | CAGCCTGCAGCCCT TGGCC (SEQ ID NO:6) | TGGAGGGGTCCCTG CAGAAG (SEQ ID NO:8) |

Insulin and glucagon mRNA expression of cultured p0, p2, and p3 cells were determined and results are shown in Table 1. Both insulin and glucagon mRNA levels were expressed at stable levels during all three cell passages.

TABLE 1

Insulin and Glucagon mRNA expression of HD394-PO through P3

| Passage Number | Insulin/Actin ratio | Glucagon/Actin ratio |
| --- | --- | --- |
| P0 | 2.6 | 1.56 |
| P2 | 0.2 | 0.46 |
| P3 | 3.0 | 3.9 |

Static Glucose Stimulation (SGS) Assay

Cells were cultured until nearly confluent. Three days prior to the SGS test, the culture medium was replaced by a medium of similar character but lacking insulin and containing only 1 g/L of glucose. The medium was changed each day for three days and the SGS test was performed on day four.

Before the test, the culture medium was collected for glucose and insulin analysis. To prepare cells for the test, cells were washed twice with Dulbecco's phosphate-buffered saline (DPBS)+0.5% BSA, incubating for 5 minutes with each wash, and then once with DPBS alone, also incubating for 5 minutes. After washing, the cells were incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation was repeated.

To perform the SGS assays, cells were incubated in 3 ml (100 mm dish) or 4 ml (T75 flask) or 2 ml (60 mm dish) KRB-60, at 37° C. for 20 minutes. The medium was aspirated and spun, and was collected for insulin assay as LG-1 (low glucose stimulated step). KRB-450+theo (KRB with 450 mg/dl glucose and 10 mM theophylline) was then added with the same volume as above, and cells were cultured under the same condition as above. The supernatant was collected for insulin assay as HG (high glucose stimulated). The cells were then incubated again with KRB-60 and the medium collected as LG-2, and another time as LG-3. The media were collected for insulin analysis, and stored at −20° C. until insulin content is determined by radioimmunoassay (RIA).

The results of the SGS test are often expressed as a stimulation index, defined as the HG insulin value divided by the LG-1 insulin value. Generally, a stimulation index of about 2 or greater is considered to be a positive result in the SGS assay.

Table 2 shows the results of the SGS test for unencapsulated cultured P3 cells. The cells had a basal insulin release level of 149.5 uU/60 mm dish/hour and a stimulated glucose level of 781.6 uU/60 mm dish/hour, a 5.2 fold increase of glucose stimulated insulin release. Furthermore, the cells returned to a normal, basal level of insulin release post stimulation. Thus, the cultured p3 cell showed normal islet-like functions.

TABLE 2

SGS test result of non-encapsulated HD394-P3 islets

| Glucose Stimulation | Low 1 (60 mg/dl) | High (450 mg/dl) | Low 2 (60 mg/dl) | Low 3 (60 mg/dl) |
| --- | --- | --- | --- | --- |
| Insulin Output | 149.5 (uU/ml) | 781.6 (uU/ml) | 348 uU/ml) | 163.7 (uU/ml) |

Example 4

Encapsulation and Aggregation of P3 Cells

An estimated 14 million cultured P2 cells were encapsulated in a mixture of high-G alginate and high M alginate to become encapsulated P3 cells. The P2 cells were suspended in 3 ml of 1.4% sodium alginate solution and then sprayed into 0.33% $CaCl_2.2H_2O$ solution through a jet-head to form cell containing alginate gel spheres approximately 700 microns in diameter. The gel spheres were soaked in the 0.33% $CaCl_2.2H_2O$ solution for 5~9 minutes, and then in 0.13% $CaCl_2.2H_2O$ solution for 8 minutes. Gel spheres were then treated with 0.1% poly-L-lysine solution for 2 minutes to form a membrane and encapsulate the cells within. The capsules were then soaked in 0.33% $CaCl_2.2H_2O$ for 1 minute. Capsules were washed with saline, soaked in 0.2% alginate for 10 minutes, and washed again with saline. The capsules were then soaked in 0.05% polylysine for 5 minutes, followed by a saline wash. The alginate gel inside the capsule was liquefied by treatment with 55 mM sodium citrate for 5 minutes. After another saline wash, the capsules were treated with 0.2% alginate for 10 minutes and then washed again with saline. To complete the encapsulation, the capsules were soaked in RPMI for 8 minutes.

After twenty-four hours, the cells in the capsules started to aggregate and form islet-like structures. The encapsulated P3 cells were cultured in M4 medium that contained 0.03 mM (30 µM) of $CaCl_2.2H_2O$ and 10% fetal calf serum in T 75 flasks. Media was changed twice a week. The encapsulated cells were maintained in vitro for 13 days, and then used for transplantation.

Example 5

Characterization of Encapsulated, Aggregated P3 Insulin Producing Cells

Within twenty-four hours after encapsulation, the proliferating pancreatic cells aggregated and displayed cellular architecture similar to that of encapsulated islets isolated directly from pancreas. In vivo and in vitro assays demonstrated the encapsulated proliferating pancreatic cells were able to function like in vitro remodeled islets.

Histology of Encapsulated, Aggregated p3 Cells Grown in Culture

Cells to be examined by immunohistochemistry may be cultured on glass chamber slides for microscopic examination. Alternatively, cells grown in conventional tissue culture or encapsulated cells may be manually removed from the culture and embedded in paraffin for sectioning. PDX-1 antibody can be made following the teachings of Leonard J. et al., Mol. Endocrinol., Oct. 7, 1993 (10) 1275–83.

Cell differentiation markers are varied and can be detected by conventional immunohistochemistry. A generally applicable protocol follows.

The staining process begins with removing chamber portion of the slides. Cells were very gently rinsed with in buffers and fixed in paraformaldehyde solution. Cells were then incubated in a blocking solution containing normal serum at room temperature. Cells were permeabilized with non-ionic detergent in blocking solution. Primary antibodies as listed below were prepared in blocking solution at appropriate dilution and added to cells and incubated. Following incubating with primary antibody, cells were rinsed in buffer and reblocked in blocking solution.

Secondary antibody prepared in blocking solution at appropriate dilution are added to the cells and incubated in the dark. Following incubation the cells were rinsed and nuclei were counterstained with Hoechst dye. Excess fluid was removed and the slides are mounted and covered with coverslides. The slides are dried and stored in the dark.

Alternatively the cells can be prepared for immunocytochemistry using the ABC method. In brief, the cells are embedded in parafin and slides with paraffin sections are dried at 37° C. overnight. The cells were deparaffinized and immersed in a hydrogen peroxide methanol solution to inhibit endogenous peroxidase activity. Slides were boiled in 0.01 citrate buffer (pH 6.0) for 30 minutes to recover certain epitopes. Slides were rinsed with buffer and blocked using normal serum at room temperature in a moist chamber.

Primary antibody prepared in blocking solution were added to the samples and incubated in a moist chamber. (Table 3 lists commonly used primary and secondary antibodies.) Slides were washed and incubated with secondary antibody prepared in blocking solution. Slides were again rinsed with buffer and incubated with Avidin-Horse Reddish Peroxides reagent or ABC complex from a commercial kit (e.g. Dako Corporation). Slides were again rinsed and incubated with diaminobenzidin developing solution; urea hydrogen peroxides in a gold wrap. After washes with distilled water, slides were immersed in Mayer's Hematoxylin for 5 minutes, then kept slides in running tap water until water turned colorless and nuclei were blue. Slides were dehydrated and mounted for viewing.

For histological analysis, aggregates within microcapsules were immunostained for CK-19, PDX-1, and endocrine hormones. Results are shown in FIG. 1A. CK-19 staining revealed a single layer of CK-19 positive cells that resembled basal layers of epithelia surrounding an interior mass of cells. The interior mass of cells showed clear staining for insulin, somatostatin, and glucagon. (FIGS. 1B–D) Thus, the staining pattern of the encapsulated p3 aggregates showed cellular architecture similar to that of remodeled islets.

In vitro Function of Encapsulated p3 Cells After Aggregation

Figure 3:
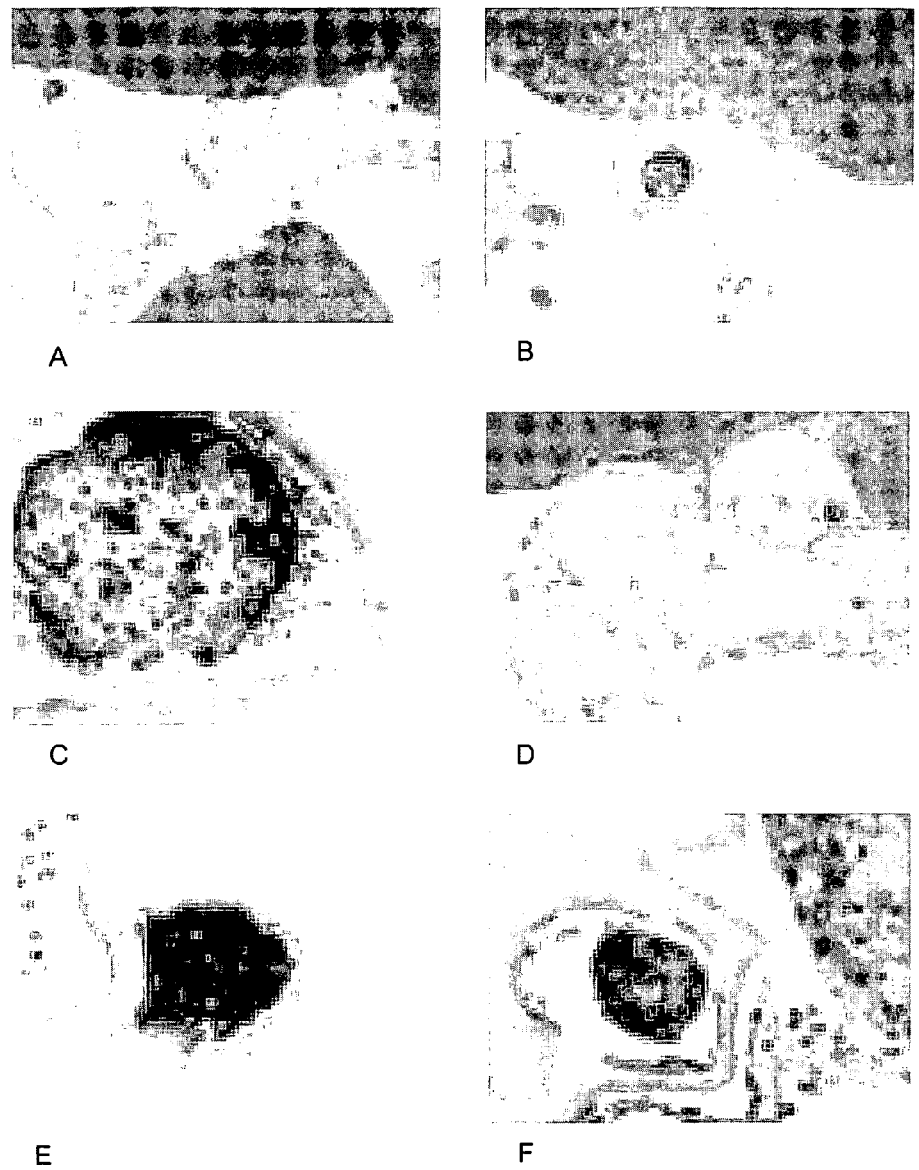
FIG. 3.

In vitro function of the encapsulated p3 aggregates was determined by SGS assay (Table 4). The cells had basal insulin release level of 3.7 uU/capsule/hour and a stimulated glucose release level of 2.3 uU/capsule/hour. The rate was lower than that of cultured p3 cells. One explanation of the muted response is that alginate binds to insulin. The SGS test was performed after the cells were encapsulated, but before the insulin binding capacity of the alginate had been satisfied. The binding of alginate to insulin was shown by the presence of insulin staining by alginate surrounding insulin-producing cells (FIG. 3E).

TABLE 4

SGS test of encapsulated HD394-P3 islets

| Glucose Stimulation | Low 1 (60 mg/dl) | High (450 mg/dl) | Low 2 (60 mg/dl) | Low 3 (60 mg/dl) |
|---|---|---|---|---|
| Insulin Output | 3.7 (uU/ml) | 2.3 (uU/ml) | 3.1 (uU/ml) | 1.6 (uU/ml) |

In vivo Function of Encapsulated p3 Cells After Aggregation

To determine the in vivo function of encapsulated p3 aggregates, the encapsulated cells were transplanted into an STZ induced diabetic SCID mouse. The experimental animals (SCID mice) were made diabetic with single intrap-

TABLE 3

The primary antibodies that are currently in use and the secondary Abs that are used in conjunction with them.

| NAME: | Primary Dilutions | | Conc. (mg/mL) | Vendor | Second. NAME: | Second. Dilutions |
|---|---|---|---|---|---|---|
| INS | 1:400 | guinea pig | 7.8 | Dako | GAM 488 | 1:500 |
| KI 67 | 1:250 | mouse | 0.05 | Dako | GAR 488 | 1:750 |
| CK19 | 1:100 | mouse | 0.04 | Dako | GAR 594 | 1:750 |
| AMYLASE | 1:2000 | rabbit | 11 | sigma | GAGP 546 | 1:500 |
| NGN3 | 1:200 | mouse | 0.25 | Transduction | | |
| SST | 1:5000 | rabbit | 1 | Diasonin | Biotinylated Goat anti-Rabbit IgG | 1:200 |
| SST | 1:50 | mouse | .14 | Biomeda | Biotinylated Goat anti-mouse IgG | 1:200 |
| PDX | 1:1000 | rabbit | 1 | Scripps | Biotinylated Goat anti-guinea pig IgG | 1:200 |
| KS | 1:200 | mouse | 0.5 | Pharminogen* | | |
| GLUCAGON | 1:7000 | rabbit | 1 | Diasonin | | |
| B-Catenin | 1:50 | mouse | 0.25 | transduction | | |
| ACTR2 | | mouse | .20 | oncogene | | | eritoneal injection of Streptozotocin (220 mg/kg). The animals became hyperglycemic (>400 mg/dl) within one week.

To transplant the encapsulated cells, the animal's abdominal wall was sterilized. Using a 1 ml syringe and a 14-gauge angiocatheter, 800 microcapsules containing 120,000 cells were sterilely implanted into the peritoneal cavity of the diabetic mouse under general anesthesia.

Blood glucose and body weight were measured periodically after transplantation. The blood samples were collected from the orbit of either eye with a heparinized glass capillary. The capillary was centrifuged and plasma was collected into an eppendorf tube. Glucose levels were measured using a Beckman II glucose analyzer.

Figure 2:
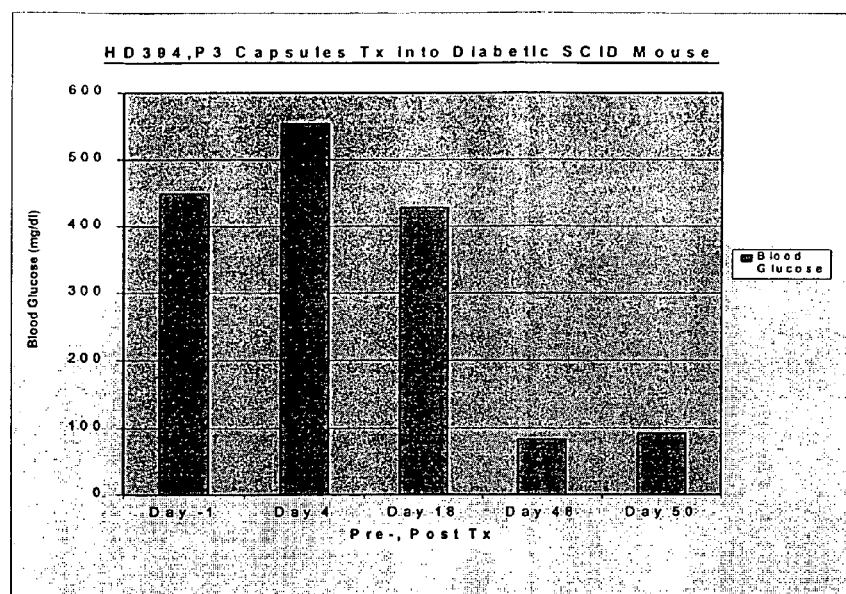
FIG. 2.

FIG. 2 shows that the encapsulated P3 cells functioned in vivo. Post-transplantation, the recipient mouse had high glucose levels for 18 days. However, on day 48 post implantation, the recipient showed a normal glucose level. The normal glucose level was confirmed by additional test on day 55 post transplant.

The transplanted encapsulated p3 aggregates were recovered from the recipient mouse for histologic analysis. The transplanted grafts and biopsy from omentum, liver and kidneys were collected for histology studies. FIGS. 3A–F shows two areas of recovered aggregates at two magnifications. Immunostaining showed the presence of insulin producing cells within the encapsulated p3 aggregates post transplantation. The surrounding alginate was also insulin positive, demonstrating the insulin binding ability of alginate (FIG. 3E).

Example 6

Characterization of in vitro Remodeled Islets After Encapsulation

For comparison, the P3 pancreatic cells were compared to islets cells isolated directly from pancreas, which are a model system for diabetes treatment. The islets cells adopt a recognizable architecture when encapsulated in alginate microcapsules shortly after isolation from pancreas. The encapsulated islet cells were maintained in culture and retained functional islet activity as measured by insulin expression and the SGS test. The encapsulated islets cells also demonstrated in vivo when function when transplanted into diabetic rats.

Encapsulation of in vitro Remodeled Islets

Human islets were isolated from donor pancreas as described above, and were at least 60% pure. Before encapsulation, the freshly isolated islets were maintained in suspension culture in M7 media with serum from 4 to 48 hours in non-adhesive Fenwall culture bags. Following encapsulation, encapsulated islets were maintained in culture for up to two and a half years. Two populations of encapsulated islets that had been maintained in culture for 6 months (HD 302) and 28 months (HD 314) were analyzed.

Figure 4:
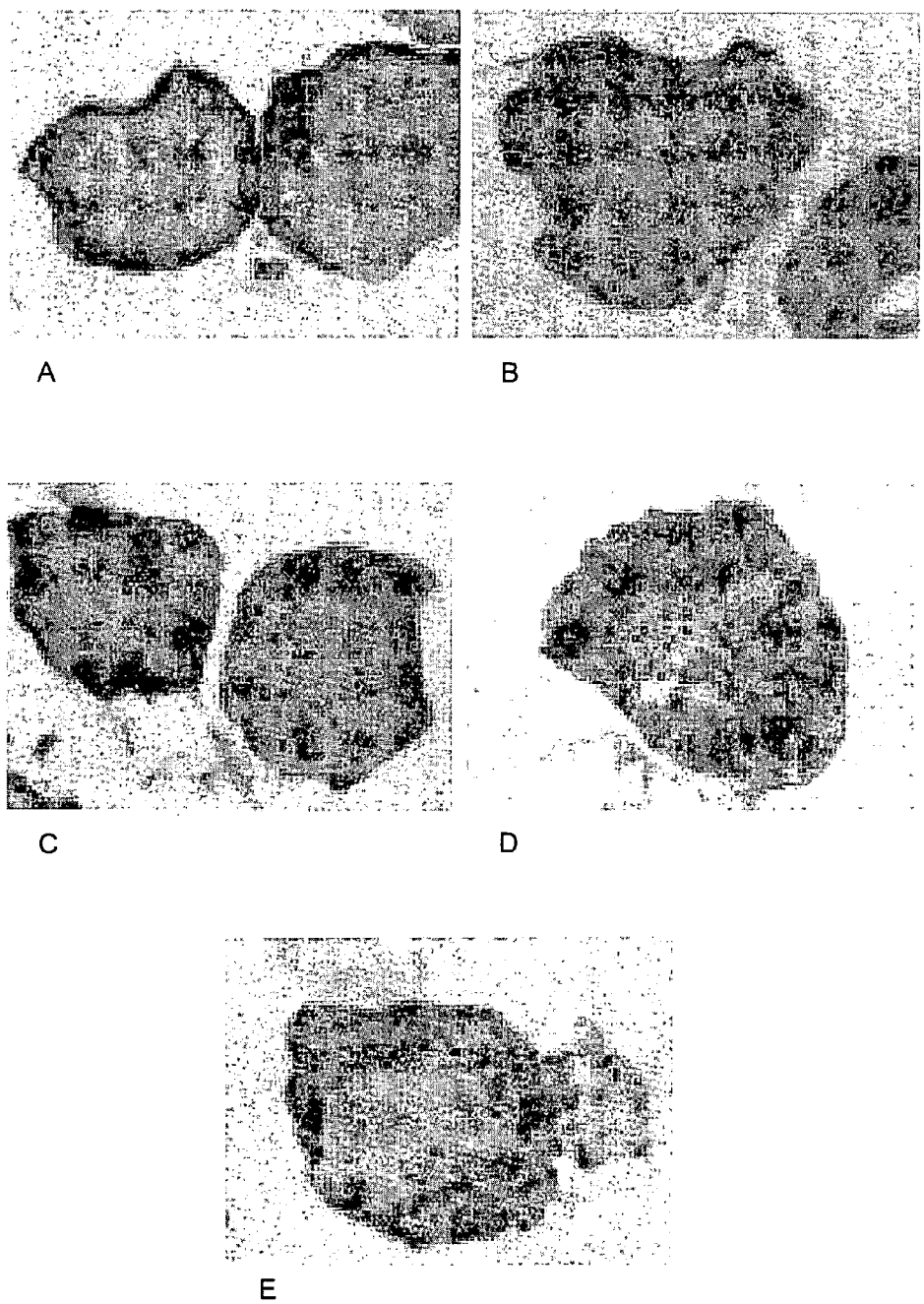
FIG. 4.
Figure 5:
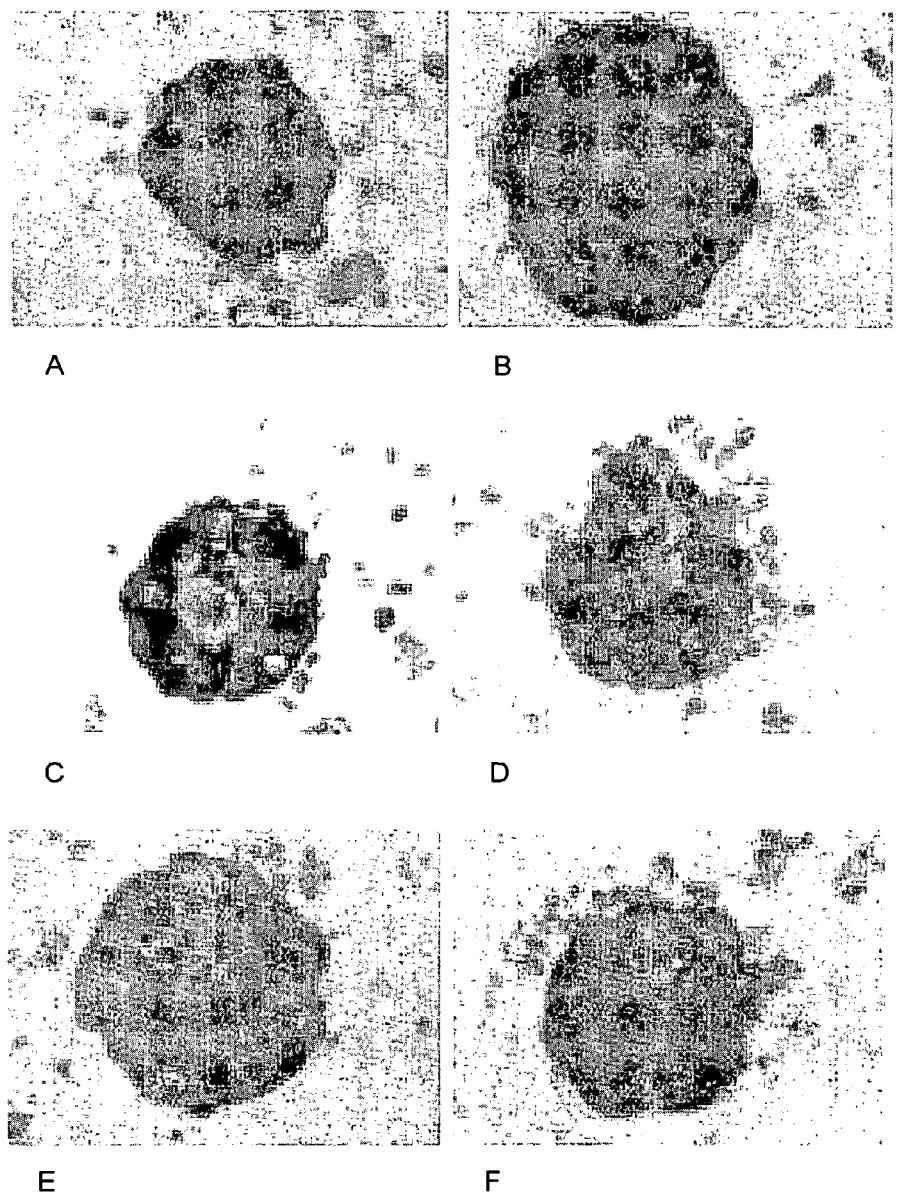
FIG. 5.

Capsules were fixed and sectioned for histological analysis, as described above. Cells within the capsules were stained for CK-19, PDX-1, endocrine hormones and amylase (FIGS. 4, A–E for 6 months islets and FIGS. 5A–F for 28 month islets).

CK-19 staining revealed an obvious difference between native and encapsulated islets. CK-19 positive cells in native islets were weakly stained and without recognizable organized cellular structure. In contrast, there was a single layer of CK-19 positive cells that surrounding the in vitro maintained islets. This difference in cellular structure indicated that the islets had remodeled after isolation from the pancreas and in vitro culture. The unique single layer structure of CK-19 positive cells from remodeled islets resembled basal layers of epithelia. Staining of endocrine hormones showed insulin, glugagons, and somatostatin positive cells were present in the inside cell mass surrounded by CK-19 positive cells.

The CK-19 positive cells were also largely PDX-1 positive, suggesting that they were pancreatic progenitor cells as reported by B. Weir (Bonner-Weir, et al. *PNAS USA* 97:7999–8004 (2000)). The surrounding CK-19, PDX1-positive cell layer seemed to diminish in number and staining intensity with time. (Compare FIGS. 2 and 3.)

Encapsulation of in vitro Remodeled Islets, in vitro Function

The in vitro function of encapsulated islets that had been maintained in culture for 9 months (HD 357) was assayed using the static glucose stimulation (SGS) assay, which measures the ability of the cells to secrete insulin in response to different glucose levels.

Each microcapsule had approximately 0.75 islet equivalents. The results are shown in Table 5. The SGS test showed basal insulin release of 17 uU/islet EQ/hour and stimulated insulin release of 73 uU/islet EQ/hour. The stimulation index was 4.

TABLE 5

Pre-Transplant SGS test for encapsulated HD357 islets, insulin output (uU/ml)

| Sample | Low (60 mg/dl) | High (450 mg/dl) | Low (60 mg/dl) |
|---|---|---|---|
| 1 | 17 | 73 | 23 |
| 2 | 16 | 67 | 24 |
| 3 | 18 | 79 | 25 |
| M + SD | 17 + 1 | 73 + 6 | 24 + 1 |

In vivo Function of in vitro Remodeled Islets

Figure 6:
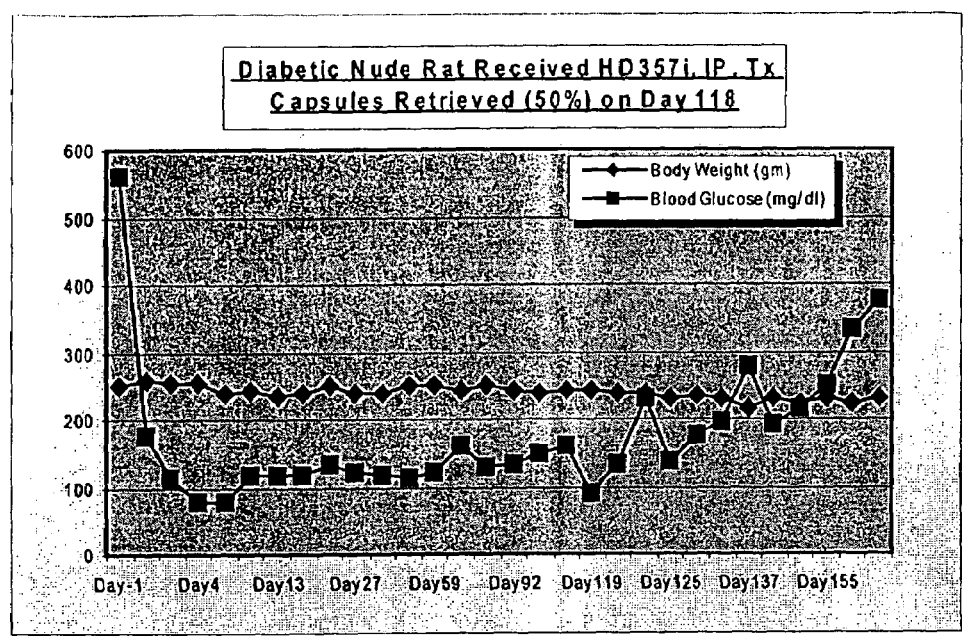
FIG. 6.

The in vivo function of encapsulated islets maintained in culture for 9 months (HD 357) was assayed by transplantation into STZ induced diabetic nude rats (FIG. 6). In rat 1, the blood glucose level decreased from a pre-transplant level of 459 mg/dl to 99 mg/dl within two days of transplantation. In rat 2, the blood glucose level decreased from a pre-transplant level of 561 mg/dl to 79 mg/dl within two days.

Figure 7:
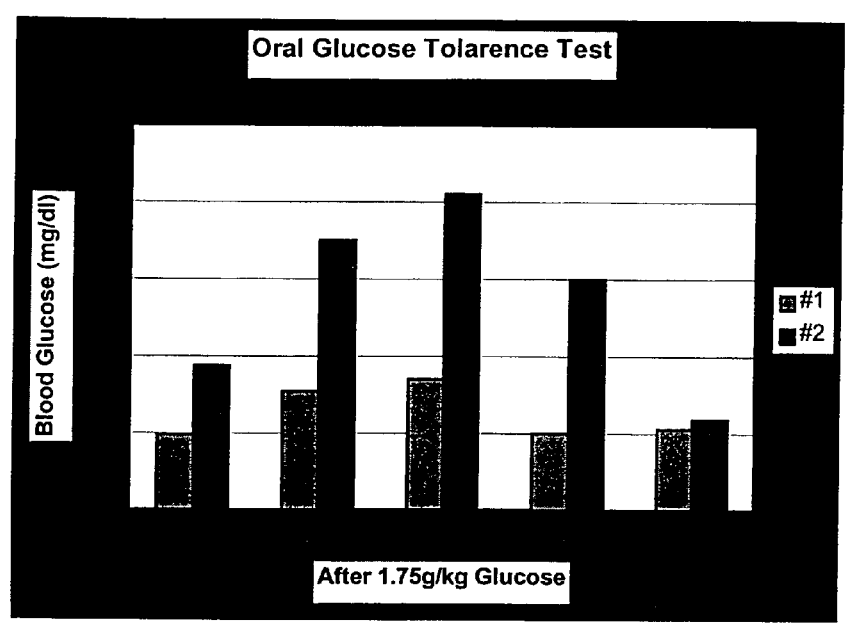
FIG. 7.

Rats were given an oral glucose tolerance test (OGTT) on day 35 post transplantation. The animals were fasted overnight, or for about 10 to 16 hours. After fasting, a blood sample was taken for plasma glucose measurement (Sample 0). Animals were fed 1.75 gm/kg glucose P.O. (45% solution). Blood samples were collected at 30 minutes (Sample 1), one hour (Sample 2), ninety minutes (Sample 3), and two hours (Sample 4) after feeding. Blood samples were drained via tail vein puncture and heparinized capillaries were used for blood collection and plasma separation. Blood glucose was measured using Beckman II glucose analyzer. Both transplanted rats performed normally, or nearly so, when given an OGTT on day 35 post transplantation (FIG. 7). For comparison, normal values are found in Table 6.

TABLE 6

Normal Values for Oral Glucose Tolerance Test

| Blood Sample | Time of Collection | Normal Range of Blood Glucose |
|---|---|---|
| 0 | Fasting | 70–105 mg/kg, <140 mg/kg |
| 1 | 30 minutes | 110–170 mg/kg, <200 mg/kg |

TABLE 6-continued

Normal Values for Oral Glucose Tolerance Test

| Blood Sample | Time of Collection | Normal Range of Blood Glucose |
|---|---|---|
| 2 | 60 minutes | 120–170 mg/kg, <200 mg/kg |
| 3 | 90 minutes | 100–140 mg/kg, <200 mg/kg |
| 4 | 120 minutes | 70–120 mg/kg, <140 mg/kg |

On day 59 post-transplantation, rat 1 died of an eye infection. On day 118, 50% of the encapsulated islet graft was removed from rat 2. Soon after, the animal's blood glucose levels began to fluctuate. Blood glucose levels increased to 300 mg/dl level 43 days after removal of the graft. Ninety-three days after removal of the graft, blood glucose levels were 403 mg/dl.

The results of these recent studies further confirmed previous pre-clinical and clinical studies that encapsulated islets, isolated directly from pancreas, were functional both in vitro and in vivo.

Example 7

Characterization of Native Islets in Human Pancreas

For comparison, islets were analyzed in pancreatic tissue to determine the location and architecture of CK-19 and PDX-1 positive cells. No recognizable architecture was found associated with CK-19 and PDX-1 positive cells in pancreatic tissue.

Histological Characterization of Islets from Donor Pancreas

Figure 8:
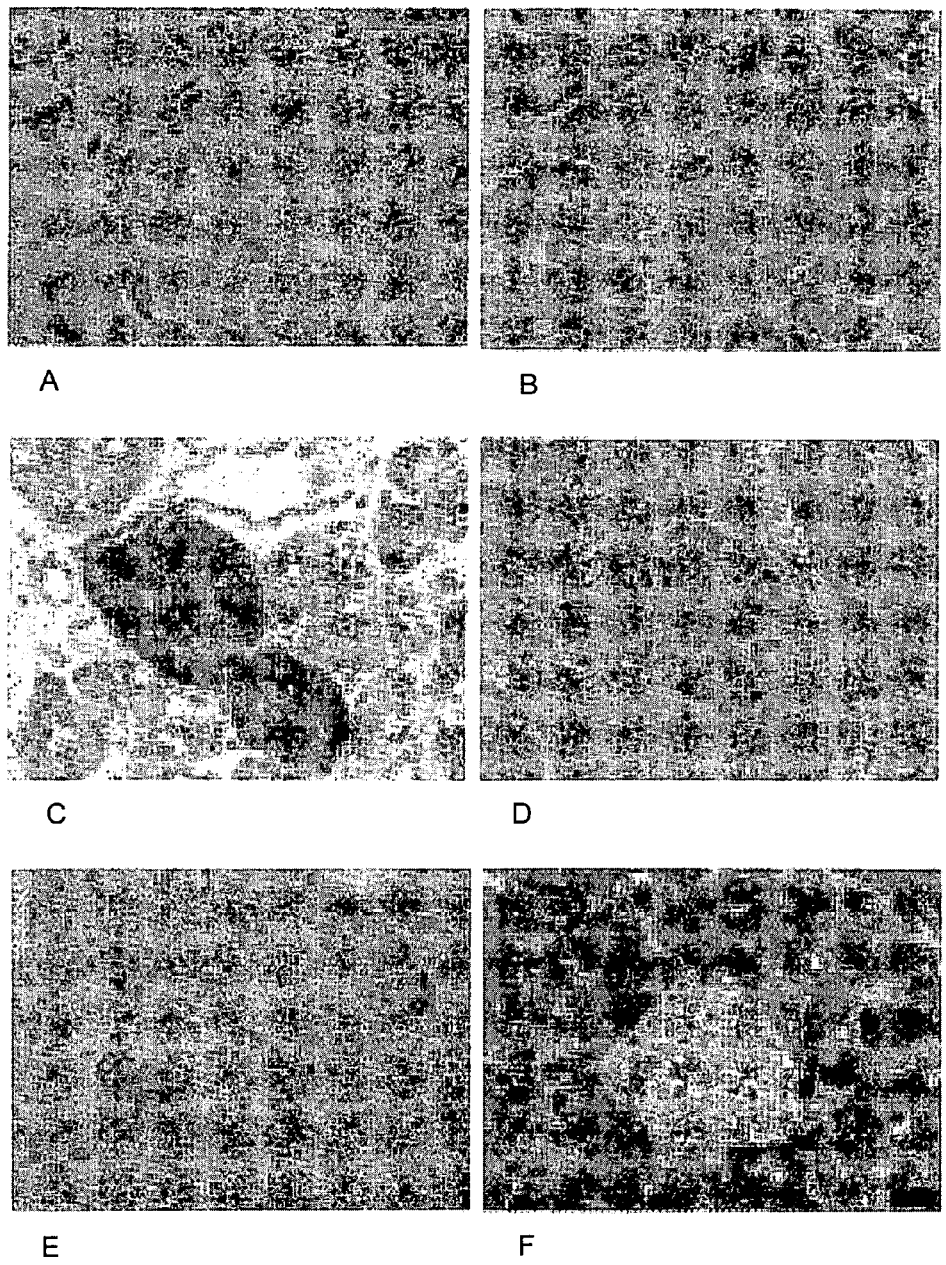
FIG. 8.

Tissue samples of donor pancreas were obtained at the time of trimming the donor pancreas for islet isolation. Samples were processed for histological characterization. Native islets and their surrounding pancreatic tissue were stained for CK-19, PDX-1, endocrine hormones, and amylase (FIGS. 8, A–F).

CK-19 staining showed that CK19 positive cells were dispersed throughout the pancreas and they were localized in the pancreatic duct as expected. Weakly stained CK19 positive cells were found inside the islets, but without a recognizable organized architecture. Staining for PDX-1 revealed many PDX-1 positive cells with nuclear staining pattern, within the islets. Direct overlap was not detected between CK19 and PDX-1 positive cells. Endocrine hormones and amylase showed typical textbook-like cell staining patterns.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of providing insulin to a mammal comprising the steps of:
(a) encapsulating a cell culture of propagating pancreatic cells having the following properties: (i) the cells have the ability to be passed from one culture vessel to a second vessel at an initial concentration of about 180 cells per square centimeter and expanded to about 1,800 cells per square centimeter; (ii) both the unexpanded and expanded cells are 90% PDX-1 positive and have an insulin:actin mRNA ratio of between 1:100 and 1000:1; and (iii) the cells mature into an aggregate of cells, comprising an encapsulating mantle of CK19-positive cells and an inner cell mass, wherein the aggregate comprises 50–5000 pancreatic cells and has a diameter of between 50 and 300 microns; and, (b) inserting the encapsulated cells into the mammal, whereby the encapsulated cells further mature to insulin secreting cells and provide insulin to the mammal.

2. A method of claim 1 wherein the mammal is a diabetic human.

3. The method of claim 1, wherein the cell culture has an insulin:actin mRNA ratio of between 1:10 and 100:1.

4. The method of claim 1, wherein the encapsulating step comprises: surrounding the cells with alginate to make a capsule, cross-linking the alginate with a divalent cation, and providing a polylysine membrane to enclose the capsule.

* * * * *

SEQUENCE LISTING

```
<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:Beta-actin
      PCR sense primer

<400> SEQUENCE: 1
cctcgccttt gccgatcc                                                        18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:insulin PCR
      sense primer

<400> SEQUENCE: 2
gccatcaagc acatcactgt                                                      20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:Beta-actin
      PCR antisense primer

<400> SEQUENCE: 3
```

-continued

```
agccacacgc agctcattgt aga                                              23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:insulin PCR
      antisense primer

<400> SEQUENCE: 4
agagggagca gatgctggta                                                  20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Beta-actin
      FITC probe

<400> SEQUENCE: 5
cccatcgagc acggcatcgt caccaa                                           26

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:insulin FITC
      probe

<400> SEQUENCE: 6
cagcctgcag cccttggcc                                                   19

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:Beta-actin
      LC RED probe

<400> SEQUENCE: 7
tgggacgaca tggagaaaat ctggcaccac                                       30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:insulin LC
      RED probe

<400> SEQUENCE: 8
tggaggggtc cctgcagaag                                                  20
```